(12) United States Patent
Merce-Vidal et al.

(10) Patent No.: US 9,963,453 B2
(45) Date of Patent: May 8, 2018

(54) SUBSTITUTED PYRAZINO[1,2-A]INDOLES AS SIGMA RECEPTOR ACTIVITY MODULATORS

(71) Applicant: LABORATORIOS DEL DR. ESTEVE S.A., Barcelona (ES)

(72) Inventors: Ramón Merce-Vidal, Barcelona (ES); José-Luis Díaz-Fernández, Manresa (ES); Carmen Almansa-Rosales, Barcelona (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days. days.

(21) Appl. No.: 14/786,241

(22) PCT Filed: Apr. 22, 2014

(86) PCT No.: PCT/EP2014/058145
§ 371 (c)(1),
(2) Date: Oct. 22, 2015

(87) PCT Pub. No.: WO2014/173901
PCT Pub. Date: Oct. 30, 2014

(65) Prior Publication Data
US 2016/0075709 A1    Mar. 17, 2016

(30) Foreign Application Priority Data

Apr. 23, 2013 (EP) .................................. 13382145

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .......................... A61K 31/4985; C07D 487/14
USPC .......................................... 514/250; 544/344
See application file for complete search history.

(56) References Cited

U.S. PATENT DOCUMENTS

| 3,317,524 | A | 5/1967 | Meier |
| 4,022,778 | A | 5/1977 | Freed |
| 5,721,245 | A | 2/1998 | Davis |
| 7,094,895 | B2 * | 8/2006 | Baraldi ............... A61K 31/496 544/295 |
| 2002/0035110 | A1 | 3/2002 | Bentley et al. |
| 2003/0171347 | A1 | 9/2003 | Matsumoto |
| 2003/0181452 | A1 | 9/2003 | Baraldi |

FOREIGN PATENT DOCUMENTS

| CN | 1452622 | 10/2003 |
| WO | WO 2007/098961 | 9/2007 |
| WO | WO 2007/121976 | 11/2007 |
| WO | WO 2008/021463 | 3/2008 |
| WO | WO 2008/055932 | 5/2008 |
| WO | WO 2008/055933 | 5/2008 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Hackam, et al. JAMA, 296(14), 2006, 1731-1732.*
CAS Registry Database, 4-[(2S)-2-amino-3-(3,4-dihydropyrazino[1,2-a]indol-2(1H)-yl)-3-oxopropyl]phenyl 5-isoquinolinesulfonic acid ester, RN: 1384852-61-2, Entered STN: Jul. 30, 2012, accessed on Jan. 26, 2016.*
Ambinter SARL [Online] XP-002698433, 1H-Isoindole-1,3(2H)-dione, 2-[3-(3,4-dihydropyrazino[1,2-a]indol-2 (1H)-yl)-3-oxpropyl], Sep. 1, 2011.
Ambinter SARL [Online] XP-002698434, 1H-Isoindole-1,3(2H)-dione, 2-[3-(3,4-dihydropyrazino[1,2-a]indol-2 (1H)-yl)-4-oxpropyl], Sep. 2, 2011.
Ambinter SARL [Online] XP-002698435, 1H-Isoindole-1,3(2H)-dione, 2-[3-(3,4-dihydropyrazino[1,2-a]indol-2 (1H)-yl)-2-oxpropyl], Sep. 7, 2011.
Bowen, et al., Pharmaceutical Acta Helvetiae, vol. 74, p. 211-218, 2000.
Hanner, et al., Proc. Natl. Acad. Sci. USA, vol. 93, p. 8072-8077, Jul. 1996.
Hayashi, et al., Drugs of the Future, vol. 34, No. 2, p. 137-146, 2009.
International Search Report PCT/EP2014/058145 of May 9, 2014.
Kaiser, et al., Neurotransmissions, vol. 7, No. 1, p. 1-5, 1991.
Quirion, et al., TIPS, vol. 13, p. 85-86, 1992.
Ronsisvalle, et al., Pure Appl. Chem., vol. 73, No. 9, p. 1499-1609, 2001.
Russell, et al., J. Med. Chem., vol. 35, p. 2025-2033, 1992.
Snyder, et al., Journal of Neuropsychiatry, vol. 1, No. 1, p. 7-15, Winter 1989.
Walker, et al., Pharmacological Revierws, vol. 42, No. 4, p. 355-402, 1990.

* cited by examiner

*Primary Examiner* — Douglas M Willis
(74) *Attorney, Agent, or Firm* — Hueschen and Sage

(57) ABSTRACT

The invention refers to compounds of general formula (I)

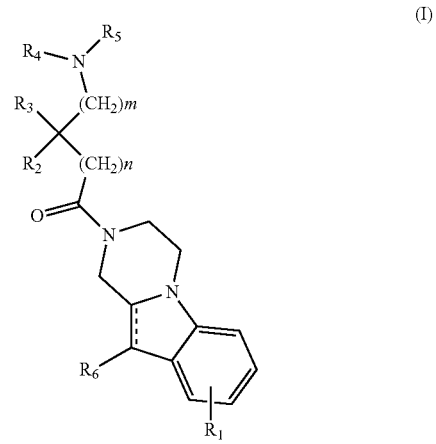

wherein the variables take the various meanings, pharmaceutical compositions containing them and their use in medicine, particularly in pain therapy.

35 Claims, No Drawings

SUBSTITUTED PYRAZINO[1,2-A]INDOLES AS SIGMA RECEPTOR ACTIVITY MODULATORS

FIELD OF THE INVENTION

The present invention relates to compounds, pharmaceutical compositions containing them and their use in medicine, particularly in pain therapy.

BACKGROUND

The search for new therapeutic agents has been greatly aided in recent years by better understanding of the structure of proteins and other biomolecules associated with target diseases. One important class of these proteins are the sigma (σ) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as SKF-10047, (+)-cyclazocine, and (+)-pentazocine and also for some narcoleptics such as haloperidol.

"The sigma receptor/s" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmacoactive drugs. SKF-10047 has nanomolar affinity for the sigma 1 (σ-1) site, and has micromolar affinity for the sigma 2 (σ-2) site. Haloperidol has similar affinities for both subtypes.

The Sigma-1 receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity. Sigma-1 receptor is of great interest in pharmacology in view of its possible physiological role in processes related to analgesia, anxiety, addiction, amnesia, depression, schizophrenia, stress, neuroprotection, psychosis and mood disorders [Kaiser et al (1991) Neurotransmissions 7 (1): 1-5], [Walker, J. M. et al, Pharmacological Reviews, 1990, 42, 355], [Bowen W. D. (2000) Pharmaceutica Acta Helvetiae 74: 211-218] and Hayashi, T. et al, Drugs of the Future 2009, 34 (2), 137].

The Sigma-2 receptor is also expressed in numerous adult mammal tissues (e.g. nervous system, immune system, endocrine system, liver, kidney). Sigma-2 receptors can be components in a new apoptosis route that may play an important role in regulating cell proliferation or in cell development. This route seems to consist of Sigma-2 receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Sigma-2 receptor ligands, specially agonists, can be used as antineoplastic agents at doses inducing apoptosis or at sub-toxic doses in combination with other antineoplastic agents to revert the resistance to the drug, thereby allowing using lower doses of the antineoplastic agent and considerably reducing its adverse effects.

Additionally, Sigma-2 receptor ligands, specially antagonists, can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find effective ligands. Different sigma receptor ligands have been reported.

For instance, WO2007098961A1 describes 4,5,6,7-tetrahydrobenzo[b]thiophene derivatives having pharmacological activity towards the sigma receptor.

Spiro[benzopyran] and spiro[benzofuran] derivatives with pharmacological activity on sigma receptors are disclosed in WO2007121976A1.

Pyrazole derivatives presenting a pyrazole group condensed with a cycloalkyl ring have been also reported as sigma ligands in WO2006021463A1.

WO2008055932A1 and WO2008055933A1 deal with 1,2,4- and 1,2,3-triazole compounds, respectively, having activity towards sigma receptors.

WO2009071657A1 also reports tricyclic triazolic compounds having activity towards sigma receptors.

U.S. Pat. No. 3,317,524A discloses substituted 1,2,3,4-tetrahydropyrazino[1,2-a]indoles and intermediates in the preparation thereof, useful as anti-inflammatory agents, as central nervous system depressants, as analgesics and as anti-convulsants.

In spite of this background, there is still a need to find further compounds that have pharmacological activity towards the sigma receptor, preferably being both effective and selective as well as having potentially good "drugability" properties, i.e. good pharmaceutical properties related to administration, distribution, metabolism and excretion.

BRIEF DESCRIPTION OF THE INVENTION

The present invention discloses novel pyrazino[1,2-a] indole compounds with great affinity to sigma receptors which might be used for the treatment and/or prophylaxis of sigma related disorders or diseases.

Specifically, it is an object of the present invention a compound of general formula (I), or a pharmaceutically acceptable salt, isomer, prodrug or solvate thereof:

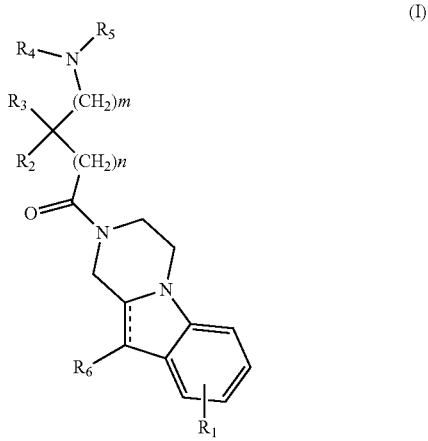

(I)

wherein
m is selected from 0, 1, 2, 3 and 4;
n is selected from 0, 1, 2, 3 and 4;
===== represents a single or double bond;
$R_1$ represents one or more optional and independent substitutions in the benzene moiety selected from the group consisting of substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen;
$R_2$ and $R_3$ are independently selected from the group consisting of hydrogen, substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, and halogen;
or $R_2$ and $R_3$ together form a substituted or unsubstituted cycloalkyl or a substituted or unsubstituted heterocyclyl;
$R_4$ and $R_5$ are independently selected from the group consisting of hydrogen, substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted, heterocyclyl, substituted or unsubstituted heterocyclylalkyl, —$COR_8$, —$C(O)OR_8$, and —$C(O)NR_8R_9$;
or $R_4$ and $R_5$ together with the bridging nitrogen atom form a substituted or unsubstituted heterocyclyl;

$R_6$ is selected from the group consisting of hydrogen, substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen;
t is selected from 0, 1 and 2;
$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl and halogen;
with the proviso that the following compounds are not included:
2-(2-(3,4-dihydropyrazino[1,2-a]indol-2(1H)-yl)-2-oxo-ethyl)isoindoline-1,3-dione,
2-(2-(3,4-dihydropyrazino[1,2-a]indol-2(1H)-yl)-2-oxopropyl)isoindoline-1,3-dione,
2-(2-(3,4-dihydropyrazino[1,2-a]indol-2(1H)-yl)-2-oxobutyl)isoindoline-1,3-dione,
[2-(3,4-dihydro-1H-pyrazino[1,2-a]indol-2-yl)-1-(4-hydroxy-benzyl)-2-oxo-ethyl]-carbamic acid tert-butyl ester,
[2-(3,4-dihydro-1H-pyrazino[1,2-a]indol-2-yl)-1-(4-hydroxy-benzyl)-2-oxo-ethyl]-methyl-carbamic acid tert-butyl ester,
[2-(8-fluoro-3,4-dihydro-1H-pyrazino[1,2-a]indol-2-yl)-1-(4-hydroxy-benzyl)-2-oxo-ethyl]-methyl-carbamic acid tert-butyl ester,
3-(2-[(trifluoroacetamido)acetyl]-1,2,3,4-tetrahydropyrazino[1,2-a]indol-10-yl]-4-(1-methyl-3-indolyl)-1H-pyrrole-2,5-dione,
3-[2-(aminoacetyl)-1,2,3,4-tetrahydropyrazino[1,2-a]indol-10-yl]-4-(1-methyl-3-indolyl)-1H-pyrrole-2,5-dione hydrochloride,
8-chloro-2-(diethylaminoacetyl)-1,2,3,4-tetrahydro-10-phenylpyrazino[1,2-a]indole,
4-(dimethylamino)-1-(10-phenyl-3,4-dihydropyrazino[1,2-a]indol-2(1H)-yl)butan-1-one, and
3-morpholino-1-(10-phenyl-3,4-dihydropyrazino[1,2-a]indol-2(1H)-yl)propan-1-one.

Another object of the invention refers to different processes for the preparation of a compound of general formula (I) as defined above, or a pharmaceutically acceptable salt, isomer, prodrug or solvate thereof.

Another object of the invention refers to a medicament or pharmaceutical composition comprising at least one compound of general formula (I) as defined above, or a pharmaceutically acceptable salt, isomer, prodrug or solvate thereof and at least one pharmaceutically acceptable excipient.

Another object of the invention refers to a compound of general formula (I) as defined above, or a pharmaceutically acceptable salt, isomer, prodrug or solvate thereof, for use as a medicament, particularly for the treatment and/or prophylaxis of a sigma receptor-mediated disease or condition.

Another object of the invention refers to the use of a compound of general formula (I) as defined above, or a pharmaceutically acceptable salt, isomer, prodrug or solvate thereof, in the manufacture of a medicament for the treatment and/or prophylaxis of a sigma receptor-mediated disease or condition.

Another object of the invention refers to a method for the treatment and/or prophylaxis of a sigma receptor-mediated disease or condition, the method comprising administering to the subject in need of such a treatment or prophylaxis a therapeutically effective amount of a compound of general formula (I) as defined above, or a pharmaceutically acceptable salt, isomer, prodrug or solvate thereof.

In one embodiment, said sigma receptor-mediated disease or condition is specifically a sigma-1 mediated disease or condition. Within the group of diseases or conditions mediated by sigma receptor for which the compounds of the invention are useful, the following may be cited: pain, diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive dyskinesia, stroke including ischemic stroke, epilepsy, stress, cancer, psychotic conditions, in particular depression, anxiety or schizophrenia; inflammation or autoimmune diseases. According to one preferred embodiment, the compounds of the invention are used for the treatment and/or prophylaxis of pain, especially neuropathic pain, inflammatory pain or other pain conditions involving allodynia and/or hyperalgesia.

These aspects and preferred embodiments thereof are additionally also defined hereinafter in the detailed description, as well as in the claims.

DETAILED DESCRIPTION OF THE INVENTION

In the context of the present invention, the following terms have the meaning detailed below.

"Alkyl" refers to a straight or branched hydrocarbon chain radical containing no unsaturation, and which is attached to the rest of the molecule by a single bond. Typical alkyl groups have from 1 to about 12, 1 to about 8, or 1 to about 6 carbon atoms, e. g., methyl, ethyl, n-propyl, i-propyl, n-butyl, t-butyl, n-pentyl, etc. If substituted by cycloalkyl, it corresponds to a "cycloalkylalkyl" radical, such as cyclopropyl methyl. If substituted by aryl, it corresponds to an "arylalkyl" radical, such as benzyl, benzhydryl or phenethyl. If substituted by heterocyclyl, it corresponds to a "heterocyclylalkyl" radical.

"Alkenyl" refers to a straight or branched hydrocarbon chain radical containing at least two carbon atoms and at least one unsaturation, and which is attached to the rest of the molecule by a single bond. Typical alkenyl radicals have from 2 to about 12, 2 to about 8 or 2 to about 6 carbon atoms. In a particular embodiment, the alkenyl group is vinyl, 1-methyl-ethenyl, 1-propenyl, 2-propenyl, or butenyl.

"Alkynyl" refers to a straight or branched hydrocarbon chain radical containing at least two carbon atoms and at least one carbon-carbon triple bond, and which is attached to the rest of the molecule by a single bond. Typical alkynyl radicals have from 2 to about 12, 2 to about 8 or 2 to about 6 carbon atoms. In a particular embodiment, the alkynyl group is ethynyl, propynyl (e.g. 1-propynyl, 2-propynyl), or butynyl (e.g. 1-butynyl, 2-butynyl, 3-butynyl).

"Cycloalkyl" refers to an alicyclic hydrocarbon. Typical cycloalkyl radicals contain from 1 to 4 separated and/or fused rings and from 3 to about 18 carbon atoms, preferably from 3 to 10 carbon atoms, such as cyclopropyl, cyclohexyl or adamantyl. In a particular embodiment, the cycloalkyl radical contains from 3 to about 6 carbon atoms.

"Aryl" refers to single and multiple ring radicals, including multiple ring radicals that contain separate and/or fused aryl groups. Typical aryl groups contain from 1 to 3 separated and/or fused rings and from 6 to about 18 carbon ring atoms, preferably from 6 to about 14 carbon ring atoms, such as phenyl, naphthyl, biphenyl, indenyl, fenanthryl or anthracyl radical.

"Heterocyclyl" include heteroaromatic and heteroalicyclic groups containing from 1 to 3 separated and/or fused rings and from 3 to about 18 ring atoms. Preferably heteroaromatic and heteroalicyclic groups contain from 5 to about 10 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothienyl, benzothiazolyl, benzoxazolyl, quinazolinyl, quinoxalinyl, naphthyridinyl, and furopyridinyl. Suitable heteroalicyclic groups in the compounds of the present invention contain one, two or three heteroatoms selected from N, O or S atoms and include, e.g., pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, oxetanyl, thietanyl, homopiperidinyl, oxepanyl, thiepanyl, azepinyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

The groups above mentioned may be substituted at one or more available positions by one or more suitable groups such as OR', =O, SR', SOR', $SO_2R'$, $OSO_2R'$, $OSO_3R'$, $NO_2$, NHR', $N(R')_2$, =N—R', N(R')COR', $N(COR')_2$, N(R')$SO_2R'$, N(R')C(=NR')N(R')R', $N_3$, CN, halogen, COR', COOR', OCOR', OCOOR', OCONHR', OCON(R')$_2$, CONHR', CON(R')$_2$, CON(R')OR', CON(R')$SO_2R'$, PO(OR')$_2$, PO(OR')R', PO(OR')(N(R')R'), $C_1$-$C_{12}$ alkyl, $C_3$-$C_{10}$ cycloalkyl, $C_2$-$C_{12}$ alkenyl, $C_2$-$C_{12}$ alkynyl, aryl, and heterocyclic group, wherein each of the R' groups is independently selected from the group consisting of hydrogen, OH, $NO_2$, $NH_2$, SH, CN, halogen, COH, COalkyl, COOH, $C_1$-$C_{12}$ alkyl, $C_3$-$C_{10}$ cycloalkyl, $C_2$-$C_{12}$ alkenyl, $C_2$-$C_{12}$ alkynyl, aryl and heterocyclic group. Where such groups are themselves substituted, the substituents may be chosen from the foregoing list.

"Halogen", "halo" or "hal" refers to bromo, chloro, iodo or fluoro.

The term "salt" must be understood as any form of a compound used in accordance with this invention in which said compound is in ionic form or is charged and coupled to a counter-ion (a cation or anion) or is in solution. This definition also includes quaternary ammonium salts and complexes of the molecule with other molecules and ions, particularly, complexes formed via ionic interactions. The definition includes in particular physiologically acceptable salts; this term must be understood as equivalent to "pharmacologically acceptable salts" or "pharmaceutically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals. These physiologically acceptable salts may be formed with cations or bases and, in the context of this invention, are understood to be salts formed by at least one compound used in accordance with the invention normally an acid (deprotonated) such as an anion and at least one physiologically tolerated cation, preferably inorganic, particularly when used on humans and/or mammals. Salts with alkali and alkali earth metals are preferred particularly, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the compound in accordance with the invention in which said compound is bonded by a non-covalent bond to another molecule (normally a polar solvent), including especially hydrates and alcoholates, like for example, methanolate. A preferred solvate is the hydrate.

Any compound that is a prodrug of a compound of formula (I) is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula (I) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers).

Any compound referred to herein is intended to represent such specific compound as well as certain variations or forms. In particular, compounds referred to herein may have asymmetric centres and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are enamine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$- or $^{14}C$-enriched carbon, or the replacement of at least one nitrogen by $^{15}N$-enriched nitrogen are within the scope of this invention.

The compounds formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

The skilled person can readily identify which substances fall under the definition of "leaving group". For the purposes of the present invention, the term "leaving group" has its commonly accepted meaning; on page 275 of March, J. "Advanced Organic Chemistry: Reactions, Mechanism and Structure", 5th Ed., Wiley-Interscience, a leaving group is defined as the part of the molecule which becomes cleaved in the reaction. Suitable leaving groups are therefore fragments of the molecule prone to being cleaved under certain reaction conditions. They may be present in the molecule from the beginning of the reaction, or may be generated in situ. For the processes disclosed herein, suitable leaving groups are commonly known and may be found in reference books, for example on pages 484-488, of March, J. "Advanced Organic Chemistry: Reactions, Mechanism and Structure", 5th Ed., Wiley-Interscience. Examples of particular leaving groups include, but are not limited to, halogen, methylsulfonyl, p-toluenesulfonyl, trifluoromethylsulfonyl, p-nitrophenyl, ethyltrifluoroacetate and the like.

As used herein, the terms "treat", "treating" and "treatment" include the eradication, removal, reversion, alleviation, modification, or control of a disease or condition after its onset.

As used herein, the terms "prevention", "preventing", "preventive" "prevent" and "prophylaxis" refer to the capacity of a therapeutic to avoid, minimize or difficult the onset or development of a disease or condition before its onset.

Therefore, by "treating" or "treatment" and/or "preventing" or "prevention", as a whole, is meant at least a suppression or an amelioration of the symptoms associated with the condition afflicting the subject, where suppression and amelioration are used in a broad sense to refer to at least a reduction in the magnitude of a parameter, e.g., symptom associated with the condition being treated. As such, the method of the present invention also includes situations where the condition is completely inhibited, e.g., prevented from happening, or stopped, e.g., terminated, such that the subject no longer experiences the condition.

The inventors of the present invention have observed that pyrazino[1,2-a]indole compounds with general formula (I) as defined above unexpectedly show an affinity for Sigma receptor ranging from good to excellent. These compounds are therefore particularly suitable as pharmacologically active agents in medicaments for the prophylaxis and/or treatment of disorders or diseases related to Sigma receptors.

In particular, pyrazino[1,2-a]indole compounds with general formula (I) as defined above acting as Sigma-1 receptor ligands are preferred.

More particularly, pyrazino[1,2-a]indole compounds with general formula (I) as defined above acting as Sigma-1 receptor antagonist ligands are preferred.

In a particular embodiment, $R_1$ represents one or more optional and independent substitutions in the benzene moiety selected from the group consisting of substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted heterocyclyl, and substituted or unsubstituted heterocyclylalkyl.

In a more particular embodiment, $R_1$ represents one o more optional and independent substitutions in the benzene moiety selected from the group consisting of substituted or unsubstituted alkyl and halogen.

Preferably, $R_1$ represents one o more optional and independent substitutions in the benzene moiety selected from the group consisting of substituted or unsubstituted $C_1$-$C_6$ alkyl and halogen. More preferably, $R_1$ represents one o more optional and independent substitutions in the benzene moiety independently selected from methyl and fluoro.

According to a particular embodiment, $R_1$, in the compounds of general formula (I), represents from one to three (one, two or three) substitutions in the benzene moiety. Further, compounds substituted at position 8 of the pyrazino [1,2-a]indol ring have been found to be particularly appropriate.

For the sake of clarity, the usual numbering of the atoms of the pyrazino[1,2-a]indol ring is depicted below.

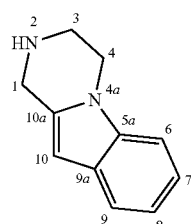

In a particular embodiment, m is selected from 0, 1 and 2 and/or n is selected from 0, 1 and 2. In a more particular embodiment, m is selected from 0 and 1 and/or n is selected from 0 and 1. Compounds of formula general (I) where the sum of m and n is 0, 1 or 2 are preferred.

In a particular embodiment, $R_2$ and $R_3$ are independently selected from the group consisting of hydrogen, substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted heterocyclyl, and substituted or unsubstituted heterocyclylalkyl.

In another particular embodiment, $R_2$ and $R_3$ are independently selected from the group consisting of hydrogen, substituted or unsubstituted alkyl and substituted or unsubstituted cycloalkyl, or $R_2$ and $R_3$ together form a substituted or unsubstituted cycloalkyl or a substituted or unsubstituted heterocyclyl.

In a more particular embodiment, $R_2$ and $R_3$ are independently selected from the group consisting of hydrogen and substituted or unsubstituted alkyl, or $R_2$ and $R_3$ together form a substituted or unsubstituted cycloalkyl.

Preferably, $R_2$ and $R_3$ are independently selected from the group consisting of hydrogen and substituted or unsubstituted C1-C6 alkyl, or $R_2$ and $R_3$ together form a substituted or unsubstituted $C_3$-$C_6$ cycloalkyl. More preferably, $R_2$ and $R_3$ are independently selected from the group consisting of hydrogen, methyl and ethyl, or $R_2$ and $R_3$ together form a cyclopropyl or cyclopentyl.

In a particular embodiment of the invention, $R_2$ and $R_3$ are independently not substituted or unsubstituted benzyl.

In a particular embodiment $R_4$ and $R_5$ are independently selected from the group consisting of hydrogen, substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted, heterocyclyl, and substituted or unsubstituted heterocyclylalkyl.

In another particular embodiment, $R_4$ and $R_5$ are independently selected from the group consisting of hydrogen, substituted or unsubstituted alkyl, and substituted or unsubstituted cycloalkyl, or $R_4$ and $R_5$ together with the bridging nitrogen atom form a substituted or unsubstituted heterocyclyl.

In another particular embodiment, $R_4$ and $R_5$ together with the bridging nitrogen atom form a heterocyclyl.group optionally substituted by a substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, or halogen.

In a more particular embodiment, $R_4$ and $R_5$ are independently selected from the group consisting of hydrogen and substituted or unsubstituted $C_1$-$C_6$ alkyl, or $R_4$ and $R_5$ together with the bridging nitrogen atom form a substituted or unsubstituted 5- to 10-membered heterocyclyl, preferably a substituted or unsubstituted 5-, 6- or 7-membered heterocyclyl. Said substituted or unsubstituted 5-, 6- or 7-membered heterocyclyl is preferably non aromatic (heteroalicyclic group).

In a particular embodiment of the invention, the heterocyclyl formed by $R_4$ and $R_5$ together with the bridging nitrogen atom is not a phthalimidyl.

Preferably, $R_4$ and $R_5$ are independently selected from the group consisting of hydrogen and substituted or unsubstituted methyl or ethyl, or $R_4$ and $R_5$ together with the bridging nitrogen atom form a substituted or unsubstituted azepanyl, diazepanyl, oxazepanyl, piperidinyl, piperazinyl, tetrahydro pyrrolyl or morpholinyl. Particular heterocyclyl radicals formed by $R_4$ and $R_5$ together with the bridging nitrogen atom are 4-methylpiperazin-1-yl, 3,5-dimethylpiperazin-1-yl, 4-acetylpiperazin-1-yl, 4-cyclohexylpiperazin-1-yl, (4-tetrahidro-2H-pyran-4-yl)piperazin-1-yl, 1,4'-bipiperidin-1'-yl, 4-methyl-1,4-diazepan-1-yl, 4-ethylpyperazin-1-yl, azepan-1-yl, piperidin-1-yl, 4-benzylpiperidin-1-yl, 1,4-oxazepan-4-yl, 9-methyl-3,9-diazaspiro[5,5]undecan-3-yl, 5-methylhexahydropyrrolo[3,4-c]pyrrolyl and morpholinyl.

In certain variants of the invention, $R_4$ and $R_5$ are independently not hydrogen or $R_4$ and $R_5$ are simultaneously not hydrogen.

In a particular embodiment, $R_6$ is selected from the group consisting of hydrogen and substituted or unsubstituted alkyl such as substituted or unsubstituted $C_1$-$C_6$ alkyl. Preferably, $R_6$ is selected from the group consisting of hydrogen and methyl.

In a further embodiment, $R_6$ is not substituted or unsubstituted aryl or substituted or unsubstituted heterocyclyl.

In additional preferred embodiments, the preferences described above for the different substituents are combined. The present invention is also directed to such combinations of preferred substitutions in the formula (I) above.

Particular individual compounds of the invention falling under formula (I) include the compounds listed below:

[1] 1-(3,4-dihydropyrazino[1,2-a]indol-2(1H)-yl)-2-(4-methylpiperazin-1-yl)propan-1-one
[2] 1-(3,4-dihydropyrazino[1,2-a]indol-2(1H)-yl)-2-methyl-2-(4-methylpiperazin-1-yl)propan-1-one
[3] 1-(3,4-dihydropyrazino[1,2-a]indol-2(1H)-yl)-3-(4-methylpiperazin-1-yl)butan-1-one
[4] 2-(azepan-1-yl)-1-(3,4-dihydropyrazino[1,2-a]indol-2(1H)-yl)ethanone hydrochloride
[5] 1-(3,4-dihydropyrazino[1,2-a]indol-2(1H)-yl)-2-(piperidin-1-yl)ethanone hydrochloride
[6] 2-(4-benzylpiperidin-1-yl)-1-(3,4-dihydropyrazino[1,2-a]indol-2(1H)-yl)ethanone hydrochloride
[7] 2-(azepan-1-yl)-1-(3,4-dihydropyrazino[1,2-a]indol-2(1H)-yl)propan-1-one
[8] 2-(azepan-1-yl)-1-(3,4-dihydropyrazino[1,2-a]indol-2(1H)-yl)propan-1-one maleate
[9] 1-(3,4-dihydropyrazino[1,2-a]indol-2(1H)-yl)-2-(piperidin-1-yl)propan-1-one
[10] 2-(4-benzylpiperidin-1-yl)-1-(3,4-dihydropyrazino[1,2-a]indol-2(1H)-yl)propan-1-one
[11] 1-(3,4-dihydropyrazino[1,2-a]indol-2(1H)-yl)-4-(dimethylamino)butan-1-one
[12] 2-(azepan-1-yl)-1-(8-fluoro-3,4-dihydropyrazino[1,2-a]indol-2(1H)-yl)ethanone
[13] 2-(azepan-1-yl)-1-(8-methyl-3,4-dihydropyrazino[1,2-a]indol-2(1H)-yl)propan-1-one
[14] 1-(10-methyl-3,4-dihydropyrazino[1,2-a]indol-2(1H)-yl)-2-(piperidin-1-yl)ethanone
[15] 2-(4-benzylpiperidin-1-yl)-1-(10-methyl-3,4-dihydropyrazino[1,2-a]indol-2(1H)-yl)ethanone
[16] 1-(8-fluoro-3,4-dihydropyrazino[1,2-a]indol-2(1H)-yl)-4-(piperidin-1-yl)butan-1-one
[17] 3-(azepan-1-yl)-1-(3,4-dihydropyrazino[1,2-a]indol-2(1H)-yl)propan-1-one
[18] (R)-1-(3,4-dihydropyrazino[1,2-a]indol-2(1H)-yl)-2-(4-methylpiperazin-1-yl)propan-1-one
[19] (S)-1-(3,4-dihydropyrazino[1,2-a]indol-2(1H)-yl)-2-(4-methylpiperazin-1-yl)propan-1-one
[20] 1-(3,4-dihydropyrazino[1,2-a]indol-2(1H)-yl)-4-(piperidin-1-yl)butan-1-one
[21] 4-(azepan-1-yl)-1-(8-fluoro-3,4-dihydropyrazino[1,2-a]indol-2(1H)-yl)butan-1-one
[22] 1-(3,4-dihydropyrazino[1,2-a]indol-2(1H)-yl)-4-(4-methylpiperazin-1-yl)butan-1-one
[23] 1-(8-fluoro-3,4-dihydropyrazino[1,2-a]indol-2(1H)-yl)-4-(4-methylpiperazin-1-yl)butan-1-one
[24] 2-(4-cyclohexylpiperazin-1-yl)-1-(3,4-dihydropyrazino[1,2-a]indol-2(1H)-yl)propan-1-one
[25] 2-(4-methylpiperazin-1-yl)-1-(3,4,10,10a-tetrahydropyrazino[1,2-a]indol-2(1H)-yl)propan-1-one
[26] 1-(8-fluoro-3,4-dihydropyrazino[1,2-a]indol-2(1H)-yl)-2-(4-methylpiperazin-1-yl)propan-1-one
[27] 2-(4-cyclohexylpiperazin-1-yl)-1-(8-fluoro-3,4-dihydropyrazino[1,2-a]indol-2(1H)-yl)propan-1-one
[28] 1-(8-fluoro-3,4-dihydropyrazino[1,2-a]indol-2(1H)-yl)-2-(4-methyl-1,4-diazepan-1-yl)propan-1-one
[29] 2-(4-ethylpiperazin-1-yl)-1-(8-fluoro-3,4-dihydropyrazino[1,2-a]indol-2(1H)-yl)propan-1-one
[30] 2-(2-(diethylamino)ethylamino)-1-(3,4-dihydropyrazino[1,2-a]indol-2(1H)-yl)propan-1-one
[31] 1-(3,4-dihydropyrazino[1,2-a]indol-2(1H)-yl)-2-(1,4-oxazepan-4-yl)propan-1-one
[32] (R)-2-(4-methylpiperazin-1-yl)-1-((S)-3,4,10,10a-tetrahydropyrazino[1,2-a]indol-2(1H)-yl)propan-1-one
[33] (S)-2-(4-methylpiperazin-1-yl)-1-((R)-3,4,10,10a-tetrahydropyrazino[1,2-a]indol-2(1H)-yl)propan-1-one
[34] (S)-2-(4-methylpiperazin-1-yl)-1-((S)-3,4,10,10a-tetrahydropyrazino[1,2-a]indol-2(1H)-yl)propan-1-one
[35] (R)-2-(4-methylpiperazin-1-yl)-1-((R)-3,4,10,10a-tetrahydropyrazino[1,2-a]indol-2(1H)-yl)propan-1-one
[36] 1-(3,4-dihydropyrazino[1,2-a]indol-2(1H)-yl)-2-(4-(tetrahydro-2H-pyran-4-yl)piperazin-1-yl)propan-1-one
[37] 2-(1,4'-bipiperidin-1'-yl)-1-(3,4-dihydropyrazino[1,2-a]indol-2(1H)-yl)propan-1-one
[38] 1-(3,4-dihydropyrazino[1,2-a]indol-2(1H)-yl)-2-(4-methylpiperazin-1-yl)butan-1-one
[39] 1-(3,4-dihydropyrazino[1,2-a]indol-2(1H)-yl)-2-((2-(dimethylamino)ethyl)(methyl)amino)butan-1-one
[40] 1-(3,4-dihydropyrazino[1,2-a]indol-2(1H)-yl)-2-((2-(dimethylamino)ethyl)(methyl)amino)propan-1-one
[41] 1-(3,4-dihydropyrazino[1,2-a]indol-2(1H)-yl)-2-methyl-3-(4-methylpiperazin-1-yl)propan-1-one
[42] 4-(4-methylpiperazin-1-yl)-1-(3,4,10,10a-tetrahydropyrazino[1,2-a]indol-2(1H)-yl)butan-1-one
[43] 4-(dimethylamino)-1-(3,4,10,10a-tetrahydropyrazino[1,2-a]indol-2(1H)-yl)butan-1-one
[44] 2-methyl-2-(4-methylpiperazin-1-yl)-1-(3,4,10,10a-tetrahydropyrazino[1,2-a]indol-2(1H)-yl)propan-1-one
[45] (R)-1-(3,4-dihydropyrazino[1,2-a]indol-2(1H)-yl)-2-(4-methylpiperazin-1-yl)butan-1-one
[46] (S)-1-(3,4-dihydropyrazino[1,2-a]indol-2(1H)-yl)-2-(4-methylpiperazin-1-yl)butan-1-one
[47] (R)-1-(3,4-dihydropyrazino[1,2-a]indol-2(1H)-yl)-2-methyl-3-(4-methylpiperazin-1-yl)propan-1-one
[48] (S)-1-(3,4-dihydropyrazino[1,2-a]indol-2(1H)-yl)-2-methyl-3-(4-methylpiperazin-1-yl)propan-1-one
[49] (S)-1-(3,4-dihydropyrazino[1,2-a]indol-2(1H)-yl)-3-(4-methylpiperazin-1-yl)butan-1-one
[50] (R)-1-(3,4-dihydropyrazino[1,2-a]indol-2(1H)-yl)-3-(4-methylpiperazin-1-yl)butan-1-one
[51] (R)-2-(4-cyclohexylpiperazin-1-yl)-1-((S)-3,4,10,10a-tetrahydropyrazino[1,2-a]indol-2(1H)-yl)propan-1-one

[52] (S)-2-(4-cyclohexylpiperazin-1-yl)-1-((R)-3,4,10,10a-tetrahydropyrazino[1,2-a]indol-2(1H)-yl)propan-1-one
[53] (S)-2-(4-cyclohexylpiperazin-1-yl)-1-((S)-3,4,10,10a-tetrahydropyrazino[1,2-a]indol-2(1H)-yl)propan-1-one
[54] (R)-2-(4-cyclohexylpiperazin-1-yl)-1-((R)-3,4,10,10a-tetrahydropyrazino[1,2-a]indol-2(1H)-yl)propan-1-one
[55] 1-(3,4-dihydropyrazino[1,2-a]indol-2(1H)-yl)-2-morpholinoethanone hydrochloride
[56] 1-(3,4-dihydropyrazino[1,2-a]indol-2(1H)-yl)-2-(4-methylpiperazin-1-yl)ethanone hydrochloride
[57] 1-(3,4-dihydropyrazino[1,2-a]indol-2(1H)-yl)-2-(dimethylamino)propan-1-one
[58] 1-(3,4-dihydropyrazino[1,2-a]indol-2(1H)-yl)-2-(dimethylamino)propan-1-one maleate
[59] 2-(4-acetylpiperazin-1-yl)-1-(3,4-dihydropyrazino[1,2-a]indol-2(1H)-yl)propan-1-one
[60] 1-(3,4-dihydropyrazino[1,2-a]indol-2(1H)-yl)-2-((3S,5R)-3,5-dimethylpiperazin-1-yl)propan-1-one
[61] (3,4-dihydropyrazino[1,2-a]indol-2(1H)-yl)(1-(piperidin-1-yl)cyclopropyl)methanone
[62] (8-fluoro-3,4-dihydropyrazino[1,2-a]indol-2(1H)-yl)(1-(piperidin-1-yl)cyclopropyl)methanone
[63] 1-(3,4-dihydropyrazino[1,2-a]indol-2(1H)-yl)-2-(9-methyl-3,9-diazaspiro[5.5]undecan-3-yl)propan-1-one
[64] (3,4-dihydropyrazino[1,2-a]indol-2(1H)-yl)(1-(4-methylpiperazin-1-yl)cyclopentyl)methanone
[65] (1-(4-methylpiperazin-1-yl)cyclopentyl)(3,4,10,10a-tetrahydropyrazino[1,2-a]indol-2(1H)-yl)methanone
[66] 2-(piperazin-1-yl)-1-(3,4,10,10a-tetrahydropyrazino[1,2-a]indol-2(1H)-yl)propan-1-one
[67] 2-(4-acetylpiperazin-1-yl)-1-(3,4,10,10a-tetrahydropyrazino[1,2-a]indol-2(1H)-yl)propan-1-one
[68] 1-(3,4-dihydropyrazino[1,2-a]indol-2(1H)-yl)-2-((3aR,6aS)-5-methylhexahydropyrrolo[3,4-c]pyrrol-2(1H)-yl)butan-1-one or a pharmaceutically acceptable salt, solvate or prodrug thereof.

The compounds of general formula (I) can be obtained by available synthetic procedures. For instance, they can be prepared in accordance with the following general procedures:

Method A

Process for the synthesis of a compound of general formula (I) as defined above, or a pharmaceutically acceptable salt, isomer, prodrug or solvate thereof, the process comprising the reaction between a compound of general formula (II)

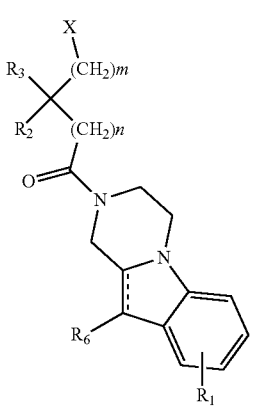

(II)

where m, n, =====, $R_1$, $R_2$, $R_3$ and $R_6$ have the meanings as in general formula (I) and X is a suitable leaving group, with a compound of general formula (III)

(III)

where $R_4$ and $R_5$ have the meanings as in general formula (I).

Compounds of general formula (II) may be prepared in turn by reaction between a compound of general formula (IV)

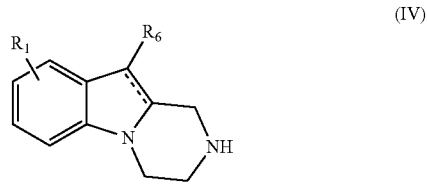

(IV)

where =====, $R_1$ and $R_6$ have the meanings as in general formula (I), with a compound of general formula (V)

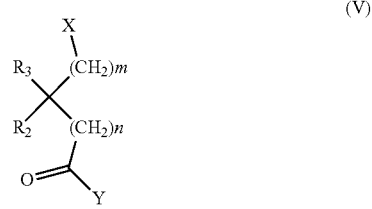

(V)

where m, n, $R_2$ and $R_3$ have the meanings as in general formula (I) and X and Y independently represent a suitable leaving group.

The above reactions can be performed in the presence of a suitable base and an organic solvent. Examples of bases include, but are not limited to, inorganic bases such as hydroxides, carbonates and sulfates of alkaline metals or alkaline earth metals, and organic bases such as mono($C_1$-$C_5$ alkyl)amine, di($C_1$-$C_5$ alkyl)amine, etc. Examples of solvents include, but are not limited to, organic solvents conventionally used in the art the present invention pertains to, preferably inert organic solvents. More specifically, examples of organic solvents to be used in the present invention are ethers such as diethyl ether, tetrahydrofuran; $C_1$-$C_6$ primary alcohols such as methanol, ethanol, propanol; halogenated compounds such as chloroform, methylene chloride; nitrile compounds such as acetonitrile, etc. These reactions can be conveniently performed at a temperature between −30° C. and a reflux temperature of the solvent used. Halogens are particularly suitable leaving groups for these reactions.

Compounds of general formula (III), (IV) and (V) are commercially available or can be synthesized from commercially available products according to known methods or modified methods thereof.

Method B

Process for the synthesis of a compound of general formula (I) as defined above, or a pharmaceutically acceptable salt, isomer, prodrug or solvate thereof, the process comprising the reaction between a compound of general formula (IV):

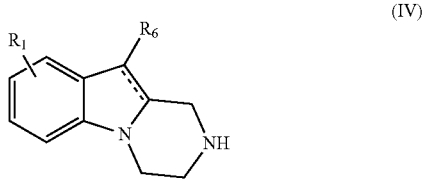
(IV)

where ----, $R_1$ and $R_6$ have the meanings as in general formula (I), with a compound of general formula (VI)

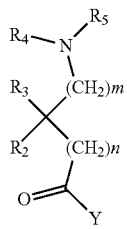
(VI)

where m, n, $R_2$, $R_3$, $R_4$ and $R_5$ have the meanings as in general formula (I) an Y is OH or a suitable leaving group.

The amidation can be performed by different routes. For instance, the amidation may be achieved by activation of the carboxylic acid with a carbodiimide, such as 1,1-dicyclohexylcarbodiimide (DCC) or 1-ethyl 3-(3-dimethylaminopropyl)carbodiimide (EDC), in the presence of a catalytic amount of an organic base, such as DMAP or HOBT in an appropriate solvent, such as dichloromethane or N,N-dimethylformamide. The amidation can be achieved as well by using acyl chlorides in the presence of an aprotic solvent, such as dichloromethane, and an organic base, such as diisopropylethylamine or triethylamine. This reaction can also be performed starting from an ester (Y=OR), when R is a good leaving group, such as p-nitrophenyl or ethyltrifluoroacetate using catalytic basic conditions.

Compounds of general formula (IV) and (VI) are commercially available or can be synthesized from commercially available products according to known methods or modified methods thereof.

Method C

Process for the synthesis of a compound of general formula (I) as defined above, or a pharmaceutically acceptable salt, isomer, prodrug or solvate thereof, the process comprising the reaction between a compound of general formula (VII)

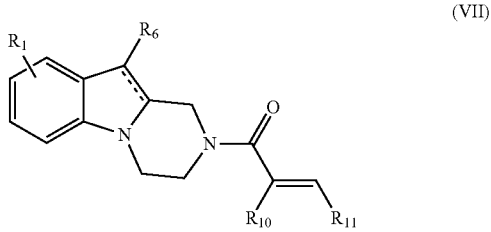
(VII)

where ----, $R_1$ and $R_6$ have the meaning as in general formula (I) and $R_{10}$ and $R_{11}$ are independently selected from the group consisting of hydrogen, substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted heterocyclyl, and substituted or unsubstituted heterocyclylalkyl;

with a compound of formula general (III)

(III)

where $R_4$ and $R_5$ have the meanings as in general formula (I).

The above mentioned process is valid for obtaining compounds of general formula (I) wherein n or m is 0 (zero) and at least one of $R_{10}$ or $R_{11}$ is hydrogen.

Compounds of general formula (VII) may be prepared in turn by reaction between a compound of general formula (IV)

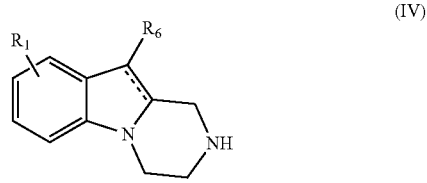
(IV)

where ----, $R_1$ and $R_6$ have the meanings as in general formula (I) with a compound of general formula (VIII)

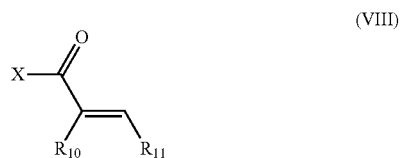
(VIII)

where $R_{10}$ and $R_{11}$ have the meanings as in general formula (VII) and X is a suitable leaving group.

The above reaction can be performed in the presence of a suitable base and an organic solvent. Examples of bases include, but are not limited to, inorganic bases such as hydroxides, carbonates and sulfates of alkaline metals or alkaline earth metals, and organic bases such as mono($C_1$-$C_5$ alkyl)amine, di($C_1$-$C_5$ alkyl)amine, etc. Examples of solvents include, but are not limited to, organic solvents conventionally used in the art the present invention pertains to, preferably inert organic solvents. More specifically, examples of organic solvents to be used in the present invention are ethers such as diethyl ether, tetrahydrofuran; $C_1$-$C_6$ primary alcohols such as methanol, ethanol, propanol; halogenated compounds such as chloroform, methylene chloride; nitrile compounds such as acetonitrile, etc. The reaction can be conveniently performed at a temperature between −30° C. and a reflux temperature of the solvent used. Halogens are particularly suitable leaving groups for this reaction.

Compounds of general formula (IV) and (VIII) are commercially available or can be synthesized from commercially available products according to known methods or modified methods thereof.

The general synthetic routes for the preparation of compounds of general formula (I) are represented in the following schemes:

obtained from the European Medicines Agency—EMA). They preferably include a "carrier, adjuvant and/or vehicle". Carriers are forms to which substances are incorporated to improve the delivery and the effectiveness of drugs. Drug carriers are used in drug-delivery systems such as the controlled-release technology to prolong in vivo drug actions, decrease drug metabolism, and reduce drug toxicity. Carriers are also used in designs to increase the effectiveness of drug delivery to the target sites of pharmacological actions (U.S. National Library of Medicine. National Institutes of Health). Adjuvant is a substance added to a drug product formulation that affects the action of the active

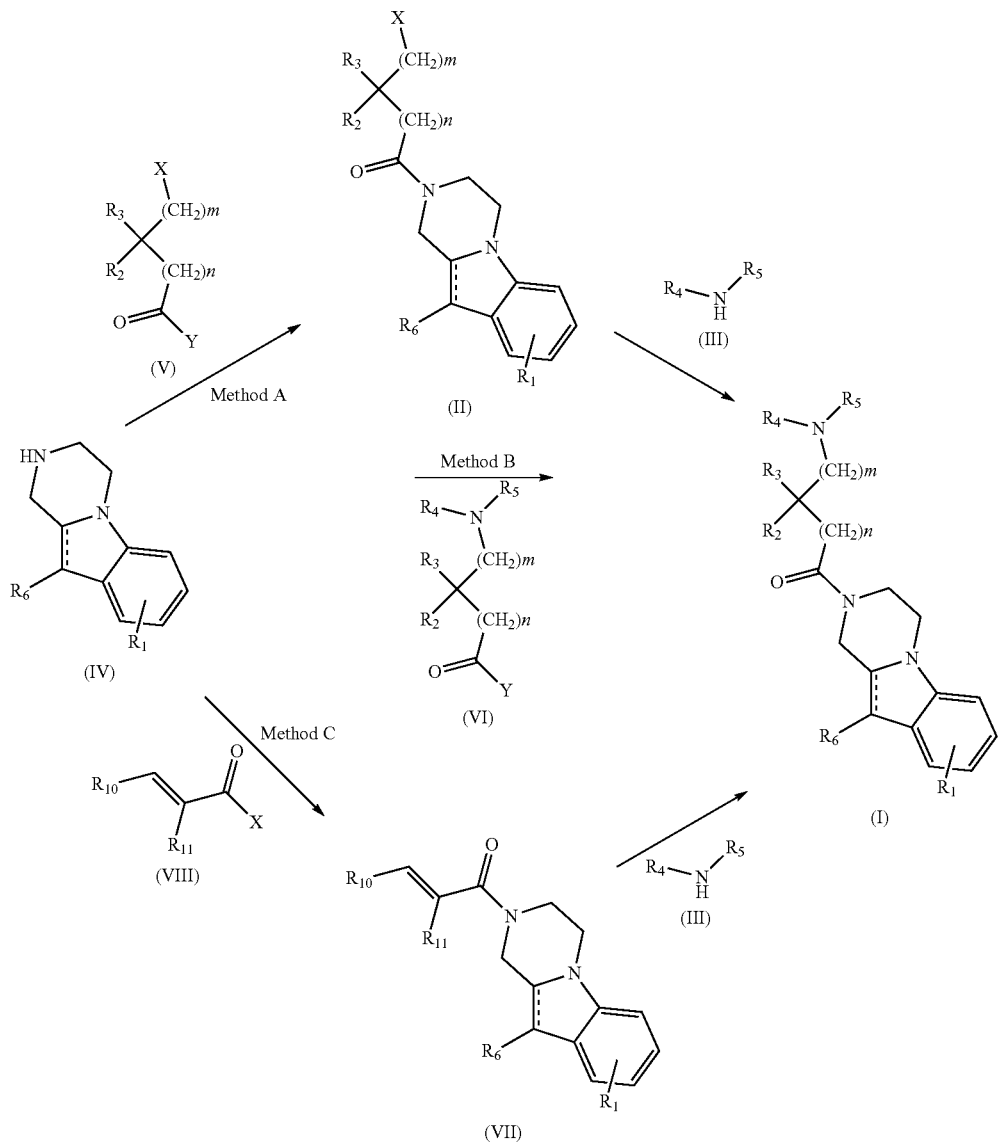

It is also an object of the invention to provide medicaments or pharmaceutical compositions comprising at least one compound of general formula (I) as defined above, or a pharmaceutically acceptable salt, isomer, prodrug or solvate thereof, and at least one pharmaceutically acceptable excipient.

The term "excipient" refers to components of a drug compound other than the active ingredient (definition ingredient in a predictable way. Vehicle is an excipient or a substance, preferably without therapeutic action, used as a medium to give bulk for the administration of medicines (Stedman's Medical Spellchecker, © 2006 Lippincott Williams & Wilkins). Such pharmaceutical carriers, adjuvants or vehicles can be sterile liquids, such as water and oils, including those of petroleum, animal, vegetable or synthetic origin, such as peanut oil, soybean oil, mineral oil, sesame oil and the like, excipients, disgregants, wetting agents or diluents. Suitable pharmaceutical carriers are described in "Remington's Pharmaceutical Sciences" by E. W. Martin. The selection of these excipients and the amounts to be used will depend on the form of application of the pharmaceutical composition.

The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application. The preferred form of rectal application is by means of suppositories.

Suitable preparations for oral applications are tablets, pills, chewing gums, capsules, granules, drops or syrups. Suitable preparations for parenteral applications are solutions, suspensions, reconstitutable dry preparations or sprays.

The pharmaceutical composition of the invention may be formulated as deposits in dissolved form or in patches, for percutaneous application. Skin applications include ointments, gels, creams, lotions, suspensions or emulsions.

Another aspect of the invention is a method for the treatment and/or prophylaxis of a sigma receptor-mediated disease or condition, the method comprising administering to the subject in need of such a treatment or prophylaxis a therapeutically effective amount of a compound of formula (I) as defined above, or a pharmaceutically acceptable salt, isomer, prodrug or solvate thereof.

Generally an effective administered amount of a compound used in the invention will depend on the relative efficacy of the compound chosen, the severity of the disorder being treated, or the age, weight or mode of administration. However, active compounds will typically be administered once or more times a day, for example 1, 2, 3 or 4 times daily, with typical total daily doses in the range of from 0.1 to 500 mg/kg/day.

Having described the present invention in general terms, it will be more easily understood by reference to the following examples which are presented as an illustration and are not intended to limit the present invention.

EXAMPLES

Method A

Example 1: 1-(3,4-dihydropyrazino[1,2-a]indol-2 (1H)-yl)-2-(4-methylpiperazin-1-yl)propan-1-one 1.1 Synthesis of 2-chloro-1-(3,4-dihydropyrazino[1, 2-a]indol-2(1H)-yl)propan-1-one

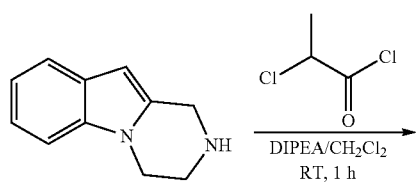

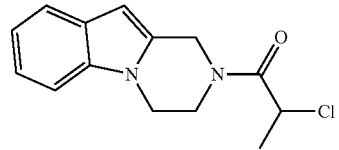

To a mixture of 1,2,3,4-tetrahydropyrazino[1,2-a]indole (200 mg, 1.16 mmol) in methylene chloride (20 mL) diisopropylethylamine (300 mg, 2, 3 mmol) was added, followed by drop-wise addition of 2-chloropropanoyl chloride (162 mg, 1.28 mmol) at 0° C. The reaction was stirred for 1 h, quenched with water, and extracted with dichloromethane. The combined organic layers were washed with water and brine, dried over magnesium sulfate and then evaporated to dryness to provide the crude product (283 mg, 93% yield) as an orange oil.

1.2 Synthesis of 1-(3,4-dihydropyrazino[1,2-a]indol-2(1H)-yl)-2-(4-methylpiperazin-1-yl)propan-1-one

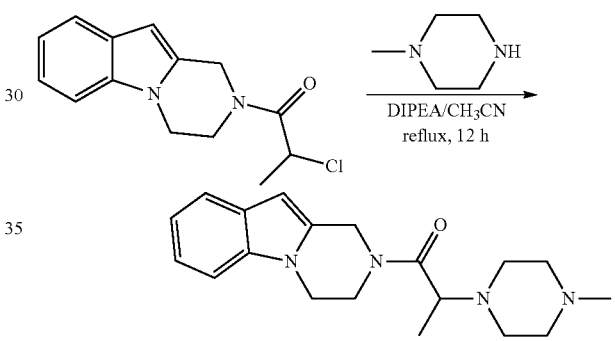

To a mixture of 2-chloro-1-(3,4-dihydropyrazino[1,2-a] indol-2(1H)-yl)propan-1-one (170 mg, 0.65 mmol) in anhydrous acetonitrile (20 mL), diisopropylethylamine (167 mg, 1.3 mmol) was added followed by drop-wise addition of methylpiperazine (130 mg, 1.3 mmol). The reaction was stirred under reflux for 12 h. After cooling and evaporation to dryness, water was added and the mixture was extracted with dichloromethane. The combined organic layers were washed with water, brine, dried over magnesium sulfate and then evaporated to dryness to provide the crude product (100 mg, 47% yield) as a brown oil.

Method B

Example 2: 1-(3,4-dihydropyrazino[1,2-a]indol-2 (1H)-yl)-2-methyl-2-(4-methylpiperazin-1-yl)propan-1-one

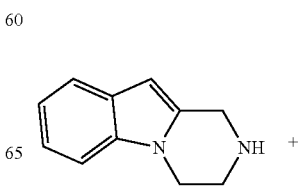

-continued

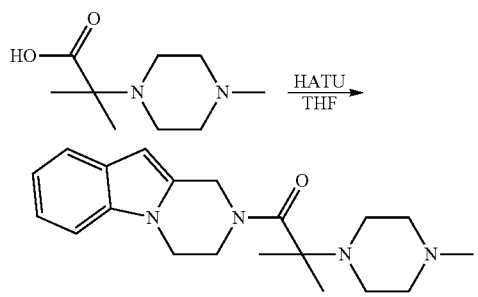

To a suspension of 2-methyl-2-(4-methylpiperazin-1-yl) propanoic acid dihydrobromide (308 mg, 0.89 mmol) in anhydrous THF (18 mL), diisopropylethylamine (225 mg, 1.74 mmol) was added and the mixture was stirred for 10 minutes. To the resulting white suspension 1,2,3,4-tetrahydro-pyrazino[1,2-a]indole (150 mg, 0.87 mmol) and 2-(1H-7-azabenzotriazol-1-yl)-1,1,3,3-tetramethyluronium hexafluorophosphate methanaminium (HATU) (519 mg, 1.36 mmol) were added and the mixture was stirred at 55-65° C. for 6 h and at rt overnight. The crude was concentrated, quenched with water and extracted with dichloromethane. The combined organic layers were sequentially washed with water and brine, dried over magnesium sulfate and then evaporated to dryness to provide a crude product that was chromatographed on silica gel to afford the title compound (155 mg, 52% yield).

Method C

Example 3: 1-(3,4-dihydropyrazino[1,2-a]indol-2(1H)-yl)-3-(4-methylpiperazin-1-yl)butan-1-one 3.1 Synthesis of 1-(3,4-dihydropyrazino[1,2-a]indol-2(1H)-yl)but-2-en-1-one

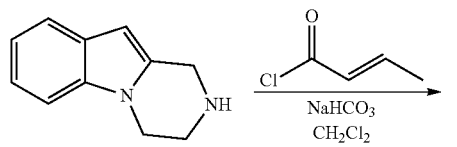

-continued

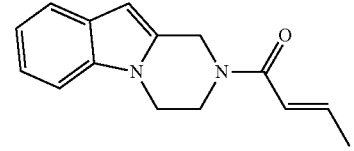

To a mixture of 1,2,3,4-tetrahydropyrazino[1,2-a]indole (2 g, 11.6 mmol) in methylene chloride (20 mL) sodium hydrogencarbonate (1.95 g, 22.3 mmol) was added followed by drop-wise addition of crotonoyl chloride (1.82 g, 17.4 mmol) at 0° C. The reaction was stirred for 2 h at room temperature, quenched with water, and extracted with dichloromethane. The combined organic layers were washed with water and brine, dried over magnesium sulfate and then evaporated to dryness to provide the crude product (1.11 g, 40% yield) as an oil.

3.2 Synthesis of 1-(3,4-dihydropyrazino[1,2-a]indol-2(1H)-yl)-3-(4-methylpiperazin-1-yl)butan-1-one

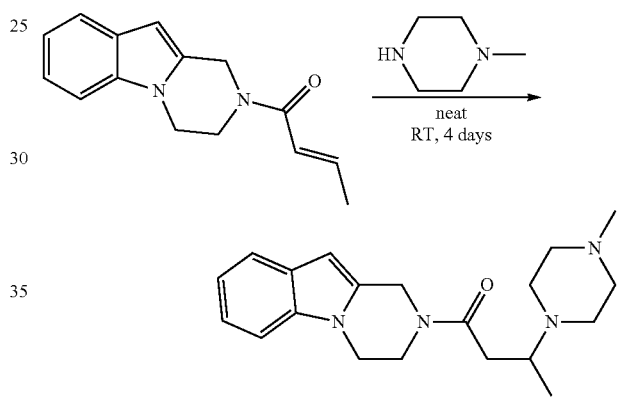

To N-methylpiperazine (3 mL), 1-(3,4-dihydropyrazino[1,2-a]indol-2(1H)-yl)but-2-en-1-one (112 mg, 0.6 mmol) was added and the solution was stirred overnight at room temperature. The reaction was stirred for 4 days until completion by TLC monitoring, quenched with water, and extracted with dichloromethane. The combined organic layers were washed with water and brine, dried over magnesium sulfate and then evaporated to dryness to provide the crude product (56 mg, 35% yield) as a solid.

Particular compounds of formula (I) are listed in table (I) below.

TABLE I

| Ex | Structure | Name | NMR |
|----|-----------|------|-----|
| 1 | 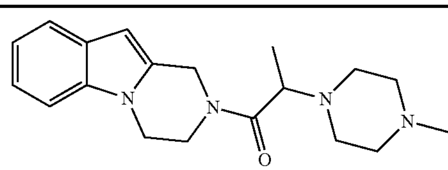 | 1-(3,4-dihydropyrazino[1,2-a]indol-2(1H)-yl)-2-(4-methylpiperazin-1-yl)propan-1-one | $^1$H NMR (CDCl$_3$) δ: 7.58 (d, J = 7.8 Hz, 1H), 7.30 (d, J = 8.2 Hz, 1H), 7.20 (t, J = 7.7 Hz, 1H), 7.13 (t, J = 7.4 Hz, 1H), 6.32 (s, 46%) and 6.29 (s, 54%) (1H), 5.21 (d, J = 16.2 Hz, 54%) and 5.18 (d, J = 17.0 Hz, 46%) (1H), 5.05 (d, J = 16.2 Hz, 54%) and 4.77 (d, J = 17.1 Hz, 46%) (1H), 4.39-3.94 (m, 4H), 3.62 (dq, J = 13.4, 6.7 Hz, 1H), 2.77-2.35 (m, 8H), 2.30 (s, 46%) and 2.26 (s, 54%) (3H), 1.26 (d, J = 6.6 Hz, 46%) and 1.23 (d, J = 6.7 Hz, 54%) (3H). |

TABLE I-continued

| Ex | Structure | Name | NMR |
|---|---|---|---|
| 2 | 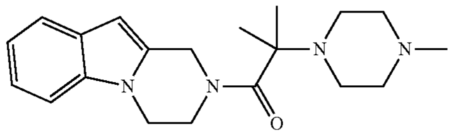 [SMILES: CN1CCN(C(C)(C)C(=O)N2CCn3c(cc4ccccc43)C2)CC1] | 1-(3,4-dihydro-pyrazino[1,2-a]indol-2(1H)-yl)-2-methyl-2-(4-methyl-piperazin-1-yl)propan-1-one | $^1$H NMR (CD$_3$OD) δ: 7.49 (d, J = 7.8 Hz, 1H), 7.32 (d, J = 8.0 Hz, 1H), 7.11 (ddd, J = 8.2, 7.1, 1.3 Hz, 1H), 7.03 (ddd, J = 8.1, 7.1, 1.2 Hz, 1H), 6.26 (s, 1H), 5.08-4.68 (m, 2H), 4.25-3.90 (m, 4H), 2.84-2.25 (m, 8H), 2.19 (s, 3H), 1.31 (s, 6H). |
| 3 | 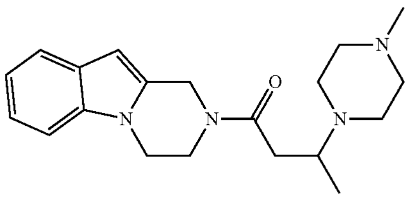 [SMILES: CC(CC(=O)N1CCn2c(cc3ccccc32)C1)N1CCN(C)CC1] | 1-(3,4-dihydro-pyrazino[1,2-a]indol-2(1H)-yl)-3-(4-methyl-piperazin-1-yl)butan-1-one | $^1$H NMR (CDCl$_3$) δ: 7.57 (d, J = 7.5 Hz, 1H), 7.29 (d, J = 8.6 Hz, 1H), 7.19 (t, J = 7.6 Hz, 1H), 7.12 (td, J = 7.4, 1.3 Hz, 1H), 6.30 (s, 1H), 4.97 (s, 35%) and 4.91 (s, 65%) (2H), 4.24-3.94 (m, 4H), 3.36-3.12 (m, 1H), 2.86-2.15 (m, 13H), 1.13 (d, J = 6.9 Hz, 35%) and 1.09 (d, J = 6.4 Hz, 65%) (3H). |
| 4 | HCl | 2-(azepan-1-yl)-1-(3,4-dihydro-pyrazino[1,2-a]indol-2(1H)-yl)ethanone hydrochloride | $^1$H NMR (DMSO) δ: 9.59 (bs, 1H), 7.52 (t, J = 6.8 Hz, 1H), 7.43 (d, J = 8.0 Hz, 1H), 7.13 (ddt, J = 9.1, 7.8, 1.7 Hz, 1H), 7.11-6.98 (m, 1H), 6.35 (s, 60%) and 6.33 (s, 40%) (1H), 4.93 (s, 60%) and 4.88 (s, 40%) (2H), 4.46 (s, 60%) and 4.42 (s, 40%) (2H), 4.29-4.20 (m, 60%) and 4.20-4.10 (m, 40%) (2H), 4.09-3.98 (m, 40%) and 3.98-3.85 (m, 60%) (2H), 3.28-3.04 (m, 4H), 1.93-1.73 (m, 4H), 1.73-1.48 (m, 4H). |
| 5 | HCl | 1-(3,4-dihydro-pyrazino[1,2-a]indol-2(1H)-yl)-2-(piperidin-1-yl)ethanone hydrochloride | $^1$H NMR (DMSO) δ: 9.52 (bs, 1H), 7.60-7.47 (m, 1H), 7.44 (d, J = 7.8 Hz, 60%) and 7.42 (d, J = 7.9 Hz, 40%) (1H), 7.19-7.08 (m, 1H), 7.08-6.98 (m, 1H), 6.36 (s, 60%), 6.34 (s, 40%) (1H), 4.93 (s, 60%) and 4.89 (s, 40%) (2H), 4.43 (s, 60%) and 4.38 (s, 40%) (2H), 4.25 (t, J = 5.3 Hz, 60%) and 4.20-4.10 (m, 40%) (2H), 4.08-4.00 (m, 40%) and 3.94 (t, J = 5.4 Hz, 60% (2H), 3.52-3.37 (m, 2H), 3.09-2.87 (m, 2H), 1.90-1.57 (m, 5H), 1.52-1.33 (m, 1H). |
| 6 | HCl | 2-(4-benzyl-piperidin-1-yl)-1-(3,4-dihydro-pyrazino[1,2-a]indol-2(1H)-yl)ethanone hydrochloride | $^1$H NMR (DMSO) δ: 9.54 (bs, 1H), 7.51 (d, J = 7.3 Hz, 1H), 7.42 (d, J = 8.4 Hz, 1H), 7.31 (t, J = 7.2 Hz, 2H), 7.25-7.16 (m, 3H), 7.12 (t, J = 7.4 Hz, 1H), 7.04 (t, J = 7.4 Hz, 1H), 6.35 (s, 68%) and 6.32 (s, 32%) (1H), 4.92 (s, 68%) and 4.86 (s, 32%) (2H), 4.55-4.32 (m, 2H), 4.23 (t, J = 5.6 Hz, 68%) and 4.14 (t, J = 5.4 Hz, 32%) (2H), 4.04 (t, J = 5.7 Hz, 32%) and 3.92 (t, J = 5.5 Hz, 68%) (2H), 3.54-3.39 (m, 2H), 3.06-2.83 (m, 2H), 2.54 (d, J = 6.3 Hz, 2H), 1.86-1.42 (m, 5H). |
| 7 | 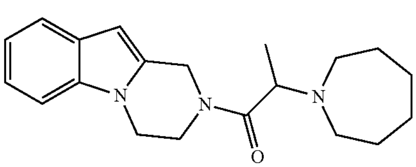 [SMILES: CC(C(=O)N1CCn2c(cc3ccccc32)C1)N1CCCCCC1] | 2-(azepan-1-yl)-1-(3,4-dihydro-pyrazino[1,2-a]indol-2(1H)-yl)propan-1-one | $^1$H NMR (CDCl$_3$) δ: 7.57 (d, J = 7.6 Hz, 1H), 7.30 (d, J = 8.0 Hz, 1H), 7.19 (t, J = 7.1 Hz, 1H), 7.18-7.06 (m, 1H), 6.32 (s, 44%) and 6.29 (s, 56%) (1H), 5.43 (d, J = 16.2 Hz, 56%) and 5.08 (d, J = 17.1 Hz, 44%) (1H), 4.95 (d, J = 16.1 Hz, 56%) and 4.85 (d, J = 17.1 Hz, 44%) (1H), 4.44-3.91 (m, 3H), 3.75-3.53 (m, 1H), 2.78-2.64 (m, 2H), 2.64-2.45 (m, 2H), 1.74-1.28 (m, 8H), 1.21 (d, J = 6.9 Hz, 44%) and 1.19 (d, J = 6.7 Hz, 56%) (3H). |

TABLE I-continued

| Ex | Structure | Name | NMR |
|---|---|---|---|
| 8 | 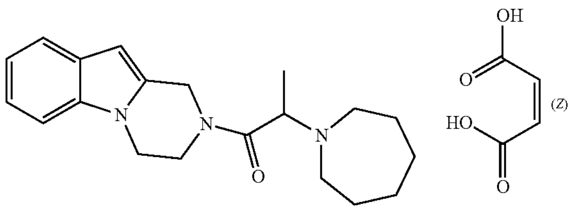 [SMILES: CC(C(=O)N1CCn2c(cc3ccccc32)C1)N1CCCCCC1 ; O=C(O)/C=C\C(=O)O] | 2-(azepan-1-yl)-1-(3,4-dihydro-pyrazino[1,2-a]indol-2(1H)-yl)propan-1-one maleate | ¹H NMR (DMSO) δ 9.34 (bs, 1H), 7.59-7.48 (m, 1H), 7.48-7.34 (m, 1H), 7.13 (t, J = 7.6 Hz, 1H), 7.04 (t, J = 7.4 Hz, 1H), 6.35 (s, 56%) and 6.33 (s, 44%) (1H), 6.05 (s, 2H), 5.18-4.63 (m, 2H), 4.36-3.83 (m, 4H), 3.57-2.94 (m, 5H), 2.01-1.69 (m, 4H), 1.69-1.52 (m, 4H). |
| 9 | 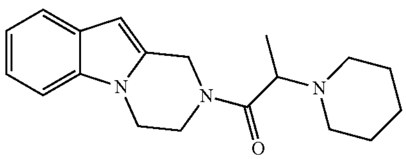 [SMILES: CC(C(=O)N1CCn2c(cc3ccccc32)C1)N1CCCCC1] | 1-(3,4-dihydro-pyrazino[1,2-a]indol-2(1H)-yl)-2-(piperidin-1-yl)propan-1-one | ¹H NMR (CDCl₃) δ: 7.58 (d, J = 7.5 Hz, 1H), 7.30 (d, J = 8.0 Hz, 1H), 7.19 (t, J = 7.3 Hz, 1H), 7.18-7.06 (m, 1H), 6.32 (s, 51%) and 6.29 (s, 49%) (1H), 5.30 (d, J = 16.3 Hz, 49%) and 5.23 (d, J = 17.1 Hz, 51%) (1H), 5.07 (d, J = 16.2 Hz, 49%) and 4.72 (d, J = 17.0 Hz, 51%) (1H), 4.44-3.90 (m, 4H), 3.65-3.46 (m, 1H), 2.61-2.26 (m, 4H), 1.59-1.28 (m, 6H), 1.22 (d, J = 6.7 Hz, 51%) and 1.20 (d, J = 6.7 Hz, 49%) (3H). |
| 10 | 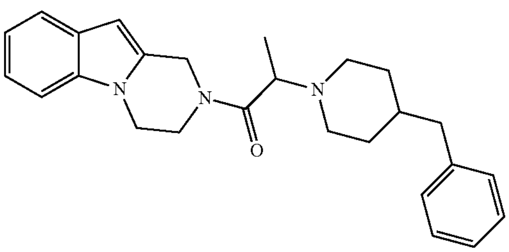 [SMILES: CC(C(=O)N1CCn2c(cc3ccccc32)C1)N1CCC(Cc2ccccc2)CC1] | 2-(4-benzyl-piperidin-1-yl)-1-(3,4-dihydro-pyrazino[1,2-a]indol-2(1H)-yl)propan-1-one | ¹H NMR (CDCl₃) δ: 7.60 (d, J = 6.8 Hz, 50%) and 7.58 (d, J = 7.2 Hz, 50%) (1H), 7.35-6.97 (m, 8H), 6.32 (s, 50%) and 6.29 (s, 50%) (1H), 5.27 (d, J = 16.3 Hz, 50%) and 5.20 (d, J = 16.9 Hz, 50%) (1H), 5.03 (d, J = 16.3 Hz, 50%) and 4.73 (d, J = 17.1 Hz, 50%) (1H), 4.40-3.90 (m, 4H), 3.68-3.46 (m, 1H), 2.80-2.27 (m, 5H), 2.21-1.97 (m, 1H), 1.73-1.37 (m, 2H), 1.36-1.05 (m, 2H), 1.20 (d, J = 6.9 Hz, 50%) and 1.17 (d, J = 6.4 Hz, 50%) (3H), 1.02-0.79 (m, 1H). |
| 11 | 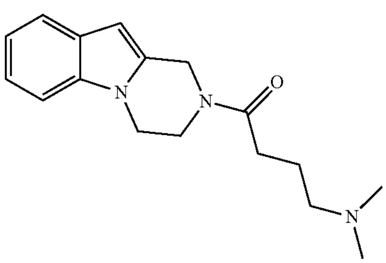 [SMILES: CN(C)CCCC(=O)N1CCn2c(cc3ccccc32)C1] | 1-(3,4-dihydro-pyrazino[1,2-a]indol-2(1H)-yl)-4-(dimethyl-amino)butan-1-one | ¹H NMR (CDCl₃) δ: 7.57 (d, J = 7.5 Hz, 1H), 7.29 (d, J = 7.7 Hz, 1H), 7.24-7.16 (m, 1H), 7.16-7.06 (m, 1H), 6.31 (s, 41%) and 6.30 (s, 59%) (1H), 4.97 (s, 41%) and 4.91 (s, 59%) (2H), 4.22-3.92 (m, 4H), 2.49 (t, J = 7.3 Hz, 2H), 2.38-2.28 (m, 2H), 2.21 (s, 41%) and 2.20 (s, 59%) (6H), 1.86 (h, J = 7.1 Hz, 2H). |
| 12 | 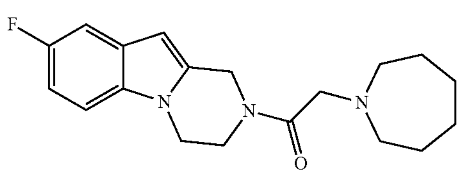 [SMILES: O=C(CN1CCCCCC1)N1CCn2c(cc3cc(F)ccc32)C1] | 2-(azepan-1-yl)-1-(8-fluoro-3,4-dihydro-pyrazino[1,2-a]indol-2(1H)-yl)ethanone | ¹H NMR (CDCl₃) δ: 7.27-7.13 (m, 2H), 6.92 (td, J = 9.1, 1.9 Hz, 1H), 6.27 (s, 50%) and 6.26 (s, 50%) (1H), 5.13 (s, 50%) and 4.94 (s, 50%) (2H), 4.21-4.02 (m, 4H), 3.41 (s, 2H), 2.75-2.55 (m, 4H), 1.71-1.46 (m, 8H). |
| 13 | 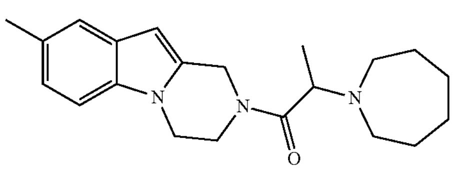 [SMILES: Cc1ccc2c(c1)cc1n2CCN(C(=O)C(C)N2CCCCCC2)C1] | 2-(azepan-1-yl)-1-(8-methyl-3,4-dihydro-pyrazino[1,2-a]indol-2(1H)-yl)propan-1-one | ¹H NMR (CDCl₃) δ: 7.36 (s, 1H), 7.18 (d, J = 8.2 Hz, 1H), 7.01 (d, J = 8.3 Hz, 1H), 6.23 (s, 43%) and 6.20 (s, 57%) (1H), 5.40 (d, J = 16.3 Hz, 57%) and 5.06 (d, J = 17.0 Hz, 43%) (1H), 4.92 (d, J = 16.0 Hz, 57%) and 4.82 (d, J = 17.1 Hz, 43%) (1H), 4.42-3.87 (m, 4H), 3.78-3.50 (m, 1H), 2.87-2.50 (m, 4H), 2.44 (s, 3H), 1.69-1.37 (m, 8H), 1.28-1.07 (m, 3H). |

TABLE I-continued

| Ex | Structure | Name | NMR |
|---|---|---|---|
| 14 | 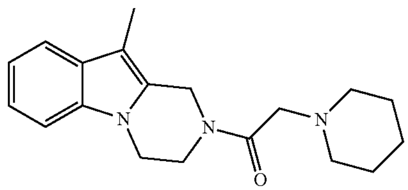 [SMILES: Cc1c2n(c3ccccc13)CCN(C(=O)CN1CCCCC1)C2] | 1-(10-methyl-3,4-dihydro-pyrazino[1,2-a]indol-2(1H)-yl)-2-(piperidin-1-yl)ethanone | $^1$H NMR (CDCl$_3$) δ: 7.54 (dd, J = 7.3, 1.4 Hz, 1H), 7.26 (d, J = 7.2 Hz, 1H), 7.19 (t, J = 7.2 Hz, 1H), 7.13 (td, J = 7.3, 1.4 Hz, 1H), 5.08 (s, 40%) and 4.89 (s, 60%) (2H), 4.19-3.95 (m, 4H), 3.25 (s, 2H), 2.42 (t, J = 5.2 Hz, 4H), 2.26 (s, 40%) and 2.25 (s, 60%) (3H), 1.62-1.48 (m, 4H), 1.48-1.34 (m, 2H). |
| 15 | 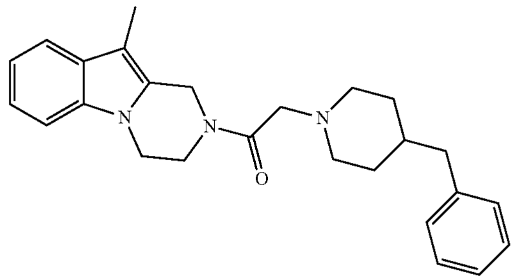 [SMILES: Cc1c2n(c3ccccc13)CCN(C(=O)CN1CCC(Cc3ccccc3)CC1)C2] | 2-(4-benzyl-piperidin-1-yl)-1-(10-methyl-3,4-dihydro-pyrazino[1,2-a]indol-2(1H)-yl)ethanone | $^1$H NMR (CDCl$_3$) δ: 7.54 (d, J = 7.7 Hz, 1H), 7.33-7.04 (m, 8H), 5.06 (s, 42%) and 4.88 (s, 58%) (2H), 4.21-3.98 (m, 4H), 3.26 (s, 2H), 2.91-2.76 (m, 2H), 2.60-2.42 (m, 2H), 2.25 (s, 3H), 2.14-1.94 (m, 3H), 1.71-1.41 (m, 3H), 1.37-1.12 (m, 1H). |
| 16 | 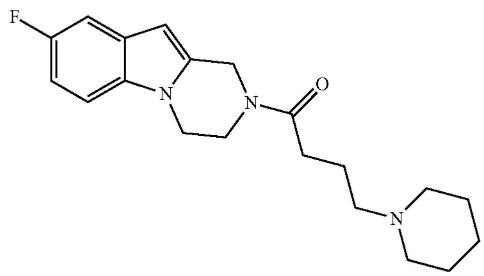 [SMILES: O=C(CCCN1CCCCC1)N1CCn2c(cc3cc(F)ccc32)C1] | 1-(8-fluoro-3,4-dihydro-pyrazino[1,2-a]indol-2(1H)-yl)-4-(piperidin-1-yl)butan-1-one | $^1$H NMR (CDCl$_3$) δ: 7.24-7.11 (m, 2H), 7.01-6.84 (m, 1H), 6.26 (s, 1H), 4.96 (s, 39%) and 4.90 (s, 61%) (2H), 4.26-3.88 (m, 4H), 2.47 (t, J = 7.5 Hz, 2H), 2.41-2.23 (m, 6H), 1.87 (h, J = 7.4 Hz, 2H), 1.60-1.49 (m, 4H), 1.50-1.33 (m, 2H). |
| 17 | 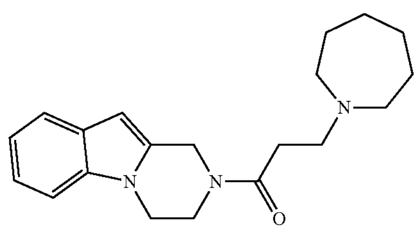 [SMILES: O=C(CCN1CCCCCC1)N1CCn2c(cc3ccccc32)C1] | 3-(azepan-1-yl)-1-(3,4-dihydro-pyrazino[1,2-a]indol-2(1H)-yl)propan-1-one | $^1$H NMR (CDCl$_3$) δ: 7.57 (d, J = 7.6 Hz, 1H), 7.29 (d, J = 8.0 Hz, 1H), 7.19 (t, J = 7.5 Hz, 1H), 7.12 (t, J = 7.3 Hz, 1H), 6.31 (s, 1H), 4.97 (s, 38%) and 4.92 (s, 62%) (2H), 4.25-3.80 (m, 4H), 3.02-2.82 (m, 2H), 2.80-2.57 (m, 6H), 1.75-1.45 (m, 8H). |
| 18 | 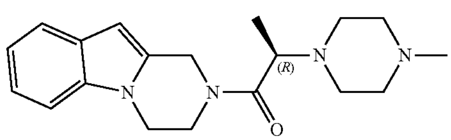 | (R)-1-(3,4-dihydro-pyrazino[1,2-a]indol-2(1H)-yl)-2-(4-methyl-piperazin-1-yl)propan-1-one | $^1$H NMR (CD$_3$OD) δ: 7.49 (d, J = 7.3 Hz, 1H), 7.34 (d, J = 7.8 Hz, 46%) and 7.32 (d, J = 7.3 Hz, 54%) (1H), 7.12 (t, J = 7.5 Hz, 1H), 7.04 (t, J = 7.5 Hz, 1H), 6.28 (s, 1H), 5.26 (d, J = 16.1 Hz, 54%) and 5.08 (d, J = 17.0 Hz, 46%) (1H), 5.03 (d, J = 16.5 Hz, 54%) and 4.79 (d, J = 17.3 Hz, 46%) (1H), 4.37-3.89 (m, 4H), 3.79 (dq, J = 16.3, 6.7 Hz, 1H), 2.70-2.32 (m, 8H), 2.26 (s, 54%) and 2.14 (s, 46%) (3H), 1.22 (d, J = 6.6 Hz, 54%) and 1.20 (d, J = 6.8 Hz, 46%) (3H). |
| 19 | 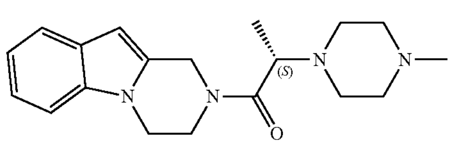 | (S)-1-(3,4-dihydro-pyrazino[1,2-a]indol-2(1H)-yl)-2-(4-methyl-piperazin-1-yl)propan-1-one | $^1$H NMR (CD$_3$OD) δ: 7.49 (d, J = 7.3 Hz, 1H), 7.34 (d, J = 7.8 Hz, 46%) and 7.32 (d, J = 7.3 Hz, 54%) (1H), 7.12 (t, J = 7.5 Hz, 1H), 7.04 (t, J = 7.5 Hz, 1H), 6.28 (s, 1H), 5.26 (d, J = 16.1 Hz, 54%) and 5.08 (d, J = 17.0 Hz, 46%) (1H), 5.03 (d, J = 16.5 Hz, 54%) and 4.79 (d, J = 17.3 Hz, 46%) (1H), 4.37-3.89 (m, 4H), 3.79 (dq, J = 16.3, 6.7 Hz, 1H), 2.70-2.32 (m, 8H), 2.26 (s, 54%) and 2.14 (s, 46%) (3H), 1.22 (d, J = 6.6 Hz, 54%) and 1.20 (d, J = 6.8 Hz, 46%) (3H). |

TABLE I-continued

| Ex | Structure | Name | NMR |
|---|---|---|---|
| 20 | 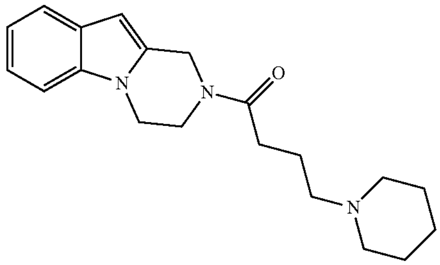 [SMILES: O=C(CCCN1CCCCC1)N1CCn2c(cc3ccccc32)C1] | 1-(3,4-dihydro-pyrazino[1,2-a]indol-2(1H)-yl)-4-(piperidin-1-yl)butan-1-one | $^1$H NMR (CDCl$_3$) δ: 7.57 (d, J = 7.7 Hz, 1H), 7.29 (d, J = 7.6 Hz, 1H), 7.19 (t, J = 7.5 Hz, 1H), 7.12 (t, J = 7.3 Hz, 1H), 6.30 (s, 1H), 4.97 (s, 39%) and 4.92 (s, 61%) (2H), 4.22-3.92 (m, 4H), 2.48 (t, J = 7.5 Hz, 2H), 2.43-2.25 (m, 6H), 1.99-1.80 (m, 2H), 1.66-1.51 (m, 4H), 1.48-1.34 (m, 2H). |
| 21 | 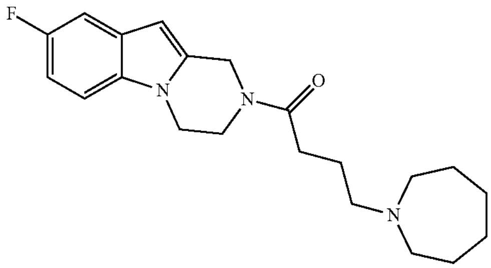 [SMILES: O=C(CCCN1CCCCCC1)N1CCn2c(cc3cc(F)ccc32)C1] | 4-(azepan-1-yl)-1-(8-fluoro-3,4-dihydro-pyrazino[1,2-a]indol-2(1H)-yl)butan-1-one | $^1$H NMR (CD$_3$OD) δ: 7.30 (dd, J = 8.8, 4.4 Hz, 1H), 7.16 (dt, J = 9.6, 2.5 Hz, 1H), 6.89 (tt, J = 9.5, 2.1 Hz, 1H), 6.31 (s, 50%) and 6.28 (s, 50%) (1H), 4.98 (s, 50%) and 4.93 (s, 50%) (2H), 4.26-4.00 (m, 4H), 2.79-2.70 (m, 2H), 2.66 (t, J = 5.2 Hz, 2H), 2.63-2.47 (m, 4H), 1.85 (dp, J = 14.9, 7.3 Hz, 2H), 1.76-1.48 (m, 8H). |
| 22 | 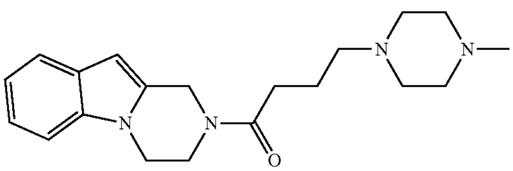 [SMILES: CN1CCN(CCCC(=O)N2CCn3c(cc4ccccc43)C2)CC1] | 1-(3,4-dihydro-pyrazino[1,2-a]indol-2(1H)-yl)-4-(4-methyl-piperazin-1-yl)butan-1-one | $^1$H NMR (CD$_3$OD) δ: 7.49 (d, J = 7.8 Hz, 1H), 7.34 (d, J = 8.1 Hz, 1H), 7.13 (ddd, J = 8.2, 7.1, 1.3 Hz, 1H), 7.10-6.98 (m, 1H), 6.31 (s, 50%) and 6.29 (s, 50%) (1H), 5.00 (s, 50%) and 4.95 (s, 50%) (2H), 4.25-4.01 (m, 4H), 2.73-2.38 (m, 12H), 2.32 (s, 50%) and 2.27 (s, 50%) (3H), 2.00-1.78 (m, 2H). |
| 23 | 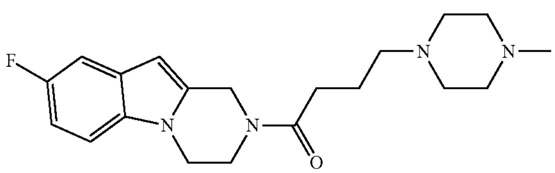 [SMILES: CN1CCN(CCCC(=O)N2CCn3c(cc4cc(F)ccc43)C2)CC1] | 1-(8-fluoro-3,4-dihydro-pyrazino[1,2-a]indol-2(1H)-yl)-4-(4-methyl-piperazin-1-yl)butan-1-one | $^1$H NMR (CD$_3$OD) δ: 7.31 (dd, J = 8.9, 4.3 Hz, 1H), 7.16 (d, J = 9.7 Hz, 1H), 6.89 (td, J =9.1, 2.5 Hz, 1H), 6.30 (s, 50%) and 6.28 (s, 50%) (1H), 4.99 (s, 50%) and 4.93 (s, 50%) (2H), 4.24-3.98 (m, 4H), 2.65-2.26 (m, 12H), 2.23 (s, 50%) and 2.20 (s, 50%) (3H), 1.95-1.74 (m, 2H). |
| 24 | 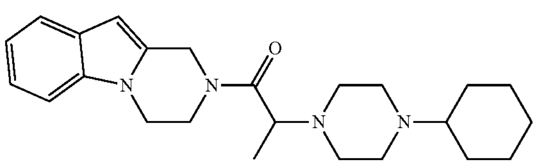 [SMILES: CC(C(=O)N1CCn2c(cc3ccccc32)C1)N1CCN(C2CCCCC2)CC1] | 2-(4-cyclohexyl-piperazin-1-yl)-1-(3,4-dihydro-pyrazino[1,2-a]indol-2(1H)-yl)propan-1-one | $^1$H NMR (CD$_3$OD) δ: 7.48 (d, J = 7.7 Hz, 1H), 7.33 (dd, J = 7.9, 2.4 Hz, 1H), 7.12 (t, J = 7.5 Hz, 1H), 7.03 (t, J = 7.4 Hz, 1H), 6.28 (s, 1H), 5.27 (d, J = 16.0 Hz, 50%) and 5.09 (d, J = 16.8 Hz, 50%) (1H), 4.98 (d, J = 16.1 Hz, 50%) and 4.78 (d, J = 17.1 Hz, 50%) (1H), 4.45-3.84 (m, 4H), 3.85-3.69 (m, 1H), 2.72-2.42 (m, 7H), 2.43-2.06 (m, 2H), 1.99-1.48 (m, 5H), 1.23 (d, J = 7.1 Hz, 50%) and 1.19 (d, J = 6.8 Hz, 50%) (3H), 1.33-0.95 (m, 5H). |
| 25 | 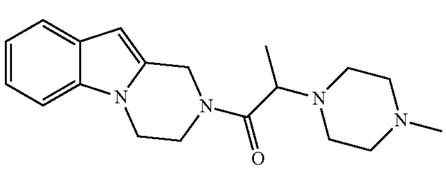 [SMILES: CC(C(=O)N1CCn2c(cc3ccccc32)C1)N1CCN(C)CC1] | 2-(4-methyl-piperazin-1-yl)-1-(3,4,10,10a-tetrahydro-pyrazino[1,2-a]indol-2(1H)-yl)propan-1-one | $^1$H NMR (CDCl$_3$) δ: 7.19-6.99 (m, 2H), 6.70 (t, J = 7.4 Hz, 1H), 6.56-6.40 (m, 1H), 4.77-4.54 (m, 1H), 4.36-4.06 (m, 1H), 3.70-3.46 (m, 3H), 3.46-2.75 (m, 4H), 2.75-2.39 (m, 9H), 2.35 (s, 41%) and 2.32 (s, 59%) (3H), 1.25 (d, J = 6.8 Hz, 41%) and 1.20 (d, J = 6.6 Hz, 59%) (3H). |

TABLE I-continued

| Ex | Structure | Name | NMR |
|----|-----------|------|-----|
| 26 | 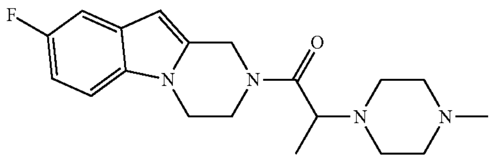 [SMILES: CC(C(=O)N1CCn2c(cc3cc(F)ccc32)C1)N1CCN(C)CC1] | 1-(8-fluoro-3,4-dihydropyrazino[1,2-a]indol-2(1H)-yl)-2-(4-methylpiperazin-1-yl)propan-1-one | ¹H NMR (CD₃OD) δ: 7.36-7.26 (m, 1H), 7.16 (ddd, J = 9.8, 4.3, 2.5 Hz, 1H), 6.89 (tt, J = 9.1, 2.3 Hz, 1H), 6.28 (s, 1H), 5.26 (d, J = 16.2 Hz, 50%) and 5.08 (d, J = 16.9 Hz, 50%) (1H), 5.02 (d, J = 16.1 Hz, 50%) and 4.78 (d, J = 16.7 Hz, 50%) (1H), 4.36-4.18 (m, 2H), 4.17-3.89 (m, 2H), 3.82 (q, J = 6.7 Hz, 50%) and 3.77 (q, J = 6.7 Hz, 50%) (1H), 2.71-2.27 (m, 8H), 2.26 (s, 50%) and 2.15 (s, 50%) (3H), 1.22 (d, J = 6.6 Hz, 50%) and 1.19 (d, J = 6.8 Hz, 50%) (3H). |
| 27 | 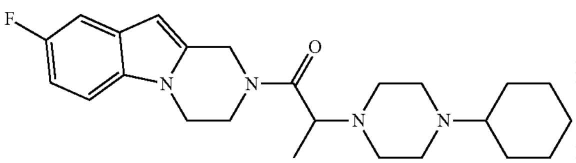 [SMILES: CC(C(=O)N1CCn2c(cc3cc(F)ccc32)C1)N1CCN(C2CCCCC2)CC1] | 2-(4-cyclohexylpiperazin-1-yl)-1-(8-fluoro-3,4-dihydropyrazino[1,2-a]indol-2(1H)-yl)propan-1-one | ¹H NMR (CDCl₃) δ: 7.19 (dd, J = 9.0, 4.7 Hz, 2H), 6.93 (td, J = 9.3, 2.4 Hz, 1H), 6.28 (s, 50%) and 6.24 (s, 50%) (1H), 5.17 (d, J = 15.6 Hz, 50%) and 5.16 (d, J = 17.2 Hz, 50%) (1H), 4.97 (d, J = 15.9 Hz, 50%) and 4.76 (d, J = 17.3 Hz, 50%) (1H), 4.37-3.83 (m, 5H), 3.71-3.45 (m, 1H), 2.63 (m, 8H), 1.80 (m, 4H), 1.26 (d, J = 6.4 Hz, 50%) and 1.23 (d, J = 6.2 Hz, 50%) (3H), 1.22-0.99 (m, 6H). |
| 28 | 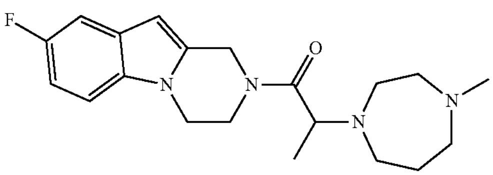 [SMILES: CC(C(=O)N1CCn2c(cc3cc(F)ccc32)C1)N1CCCN(C)CC1] | 1-(8-fluoro-3,4-dihydropyrazino[1,2-a]indol-2(1H)-yl)-2-(4-methyl-1,4-diazepan-1-yl)propan-1-one | ¹H NMR (DMSO) δ: 7.41 (td, J = 8.0, 7.6, 4.5 Hz, 1H), 7.27 (ddd, J = 9.4, 6.2, 2.7 Hz, 1H), 6.94 (tt, J = 9.0, 3.1 Hz, 1H), 6.31 (s, 1H), 5.28 (d, J = 16.3 Hz, 40%) and 4.89 (d, J = 17.7 Hz, 60%) (1H), 4.84 (d, J = 16.7 Hz, 40%) and 4.79 (d, J = 16.9 Hz, 60%) (1H), 4.33-3.63 (m, 5H), 2.81-2.55 (m, 6H), 2.16-1.92 (m, 2H), 1.82-1.53 (m, 2H), 1.06 (d, J = 6.6 Hz, 60%) and 1.04 (d, J = 6.6 Hz, 40%) (3H). |
| 29 | 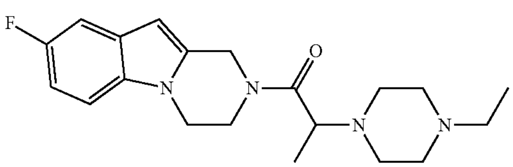 [SMILES: CCN1CCN(C(C)C(=O)N2CCn3c(cc4cc(F)ccc43)C2)CC1] | 2-(4-ethylpiperazin-1-yl)-1-(8-fluoro-3,4-dihydropyrazino[1,2-a]indol-2(1H)-yl)propan-1-one | ¹H NMR (CD₃OD) δ: 7.31 (dt, J = 9.5, 5.0 Hz, 1H), 7.16 (dt J = 9.8, 2.2 Hz, 1H), 6.89 (tt, J = 9.1, 2.3 Hz, 1H), 6.28 (s, 1H), 5.26 (d, J = 16.2 Hz, 50%) and 5.08 (d, J = 16.9 Hz, 50%) (1H), 5.02 (d, J = 16.4 Hz, 50%) and 4.78 (d, J = 17.4 Hz, 50%) (1H), 4.35-3.90 (m, 4H), 3.82 (q, J = 6.7 Hz, 50%) and 3.77 (q, J = 6.7 Hz, 50%) (1H), 2.70-2.20 (m, 8H), 2.42 (q, J = 7.2 Hz, 50%) and 2.31 (q, J = 7.2 Hz, 50%) (2H), 1.23 (d, J = 6.7 Hz, 50%) and 1.20 (d, J = 6.7 Hz, 50%) (3H), 1.08 (t, J = 7.3 Hz, 50%) and 1.01 (t, J = 7.3 Hz, 50%) (3H). |
| 30 | 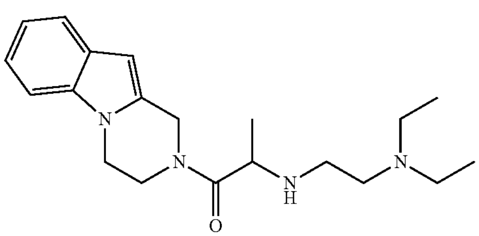 [SMILES: CCN(CC)CCNC(C)C(=O)N1CCn2c(cc3ccccc32)C1] | 2-(2-(diethylamino)ethylamino)-1-(3,4-dihydropyrazino[1,2-a]indol-2(1H)-yl)propan-1-one | ¹H NMR (CDCl₃) δ: 7.58 (d, J = 7.8 Hz, 1H), 7.30 (d, J = 7.8 Hz, 1H), 7.20 (t, J = 7.0 Hz, 1H), 7.13 (t, J = 7.4 Hz, 1H), 6.32 (s, 1H), 5.15-4.87 (m, 2H), 4.31-3.96 (m, 4H), 3.74 (q, J = 6.9 Hz, 1H), 2.77-2.38 (m, 8H), 1.31 (d, J = 6.6 Hz, 40%) and 1.25 (d, J = 6.7 Hz, 60%) (3H), 1.00 (dt, J = 11.5, 6.9 Hz, 6H). |
| 31 | 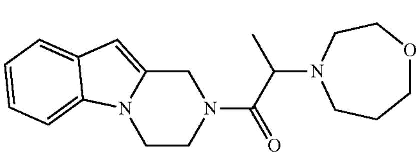 [SMILES: CC(C(=O)N1CCn2c(cc3ccccc32)C1)N1CCCOCC1] | 1-(3,4-dihydropyrazino[1,2-a]indol-2(1H)-yl)-2-(1,4- | ¹H NMR (CDCl₃) δ: 7.58 (d, J = 7.7 Hz, 1H), 7.30 (d, J = 8.2 Hz, 1H), 7.19 (t, J = 7.6 Hz, 1H), 7.13 (t, J = 7.4 Hz, 1H), 6.33 (s, 43%) and 6.30 (s, 57%) (1H), 5.34 (d, J = 16.0 Hz, 57%) and 5.13 (d, J = 17.0 Hz, 43%) (1H), 4.95 |

TABLE I-continued

| Ex | Structure | Name | NMR |
|----|-----------|------|-----|
| | | oxazepan-4-yl)propan-1-one | (d, J = 16.2 Hz, 57%) and 4.81 (d, J = 17.3 Hz, 43%) (1H), 4.44-3.90 (m, 4H), 3.78 (t, J = 5.9 Hz, 2H), 3.69 (t, J = 6.0 Hz, 2H), 3.78-3.44 (m, 1H), 2.94-2.63 (m, 4H), 1.95-1.75 (m, 2H), 1.26 (d, J = 6.7 Hz, 57%) and 1.23 (d, J = 6.1 Hz, 43%) (3H). |
| 32 | 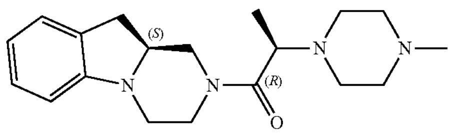 | (R)-2-(4-methyl-piperazin-1-yl)-1-((S)-3,4,10,10a-tetrahydro-pyrazino[1,2-a]indol-2(1H)-yl)propan-1-one | $^1$H NMR (CDCl$_3$) δ: 7.10 (m, 2H), 6.70 (t, J = 7.4 Hz, 1H), 6.50 (d, J = 7.7 Hz, 57%) and 6.47 (d, J = 7.7 Hz, 43%) (1H), 4.73-4.61 (m, 1H), 4.31 (d, J = 12.9 Hz, 43%) and 4.20 (d, J = 12.1 Hz, 57%) (1H), 3.64-3.46 (m, 4H), 3.11-2.96 (m, 2H), 2.87-2.75 (m, 1H), 2.70-2.35 (m, 9H), 2.31 (s, 43%) and 2.29 (s, 57%) (3H), 1.24 (d, J = 6.7 Hz, 43%) and 1.19 (d, J = 6.6 Hz, 57%) (3H). |
| 33 | 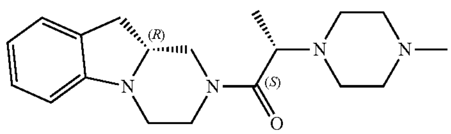 | (S)-2-(4-methyl-piperazin-1-yl)-1-((R)-3,4,10,10a-tetrahydro-pyrazino[1,2-a]indol-2(1H)-yl)propan-1-one | $^1$H NMR (CDCl$_3$) δ: 7.10 (m, 2H), 6.70 (t, J = 7.4 Hz, 1H), 6.50 (d, J = 7.7 Hz, 57%) and 6.47 (d, J = 7.7 Hz, 43%) (1H), 4.73-4.61 (m, 1H), 4.31 (d, J = 12.9 Hz, 43%) and 4.20 (d, J = 12.1 Hz, 57%) (1H), 3.64-3.46 (m, 4H), 3.11-2.96 (m, 2H), 2.87-2.75 (m, 1H), 2.70-2.35 (m, 9H), 2.31 (s, 43%) and 2.29 (s, 57%) (3H), 1.24 (d, J = 6.7 Hz, 43%) and 1.19 (d, J = 6.6 Hz, 57%) (3H). |
| 34 | 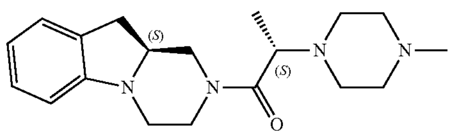 | (S)-2-(4-methyl-piperazin-1-yl)-1-3,4,10,10a-tetrahydro-pyrazino[1,2-a]indol-2(1H)-yl)propan-1-one | $^1$H NMR (CDCl$_3$) δ: 7.11 (d, J = 7.3 Hz, 1H), 7.10 (t, J = 7.5 Hz, 1H), 6.70 (t, J = 7.4 Hz, 1H), 6.49 (d, J = 7.8 Hz, 1H), 4.70 (d, J = 12.6 Hz, 64%) and 4.64 (d, J = 11.8 Hz, 36%) (1H), 4.35 (d, J = 12.6 Hz, 36%) and 4.19 (d, J = 12.0 Hz, 64%) (1H), 3.67-3.47 (m, 2H), 3.46-3.28 (m, 1H), 3.23-3.10 (m, 1H), 3.11-2.97 (m, 2H), 2.89 (td, J = 12.1, 2.9 Hz, 64%) and 2.80 (td, J = 12.2, 3.1 Hz, 36%) (1H), 2.71-2.35 (m, 9H), 2.29 (s, 36%) and 2.28 (s, 64%) (3H), 1.24 (d, J = 6.8 Hz, 36%) and 1.19 (d, J = 6.6 Hz, 64%) (3H). |
| 35 | 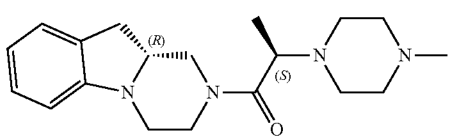 | (R)-2-(4-methyl-piperazin-1-yl)-1-((R)-3,4,10,10a-tetrahydro-pyrazino[1,2-a]indol-2(1H)-yl)propan-1-one | $^1$H NMR (CDCl$_3$) δ: 7.11 (d, J = 7.3 Hz, 1H), 7.10 (t, J = 7.5 Hz, 1H), 6.70 (t, J = 7.4 Hz, 1H), 6.49 (d, J = 7.8 Hz, 1H), 4.70 (d, J = 12.6 Hz, 64%) and 4.64 (d, J = 11.8 Hz, 36%) (1H), 4.35 (d, J = 12.6 Hz, 36%) and 4.19 (d, J = 12.0 Hz, 64%) (1H), 3.67-3.47 (m, 2H), 3.46-3.28 (m, 1H), 3.23-3.10 (m, 1H), 3.11-2.97 (m, 2H), 2.89 (td, J = 12.1. 2.9 Hz, 64%) and 2.80 (td, J = 12.2, 3.1 Hz, 36%) (1H), 2.71-2.35 (m, 9H), 2.29 (s, 36%) and 2.28 (s, 64%) (3H), 1.24 (d, J = 6.8 Hz, 36%) and 1.19 (d, J = 6.6 Hz, 64%) (3H). |
| 36 | 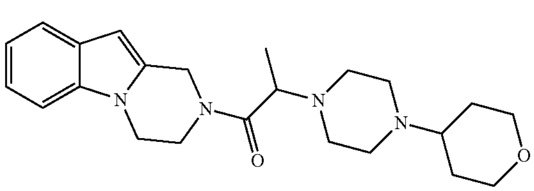 [SMILES: CC(C(=O)N1CCn2c(cc3ccccc32)C1)N1CCN(C2CCOCC2)CC1] | 1-(3,4-dihydro-pyrazino[1,2-a]indol-2(1H)-yl)-2-(4-(tetrahydro-2H-pyran-4-yl)piperazin-1-yl)propan-1-one | $^1$H NMR (CDCl$_3$) δ: 7.58 (d, J = 7.8 Hz, 44%) and 7.56 (d, J = 6.8 Hz, 56%) (1H), 7.29 (d, J = 8.0 Hz, 1H), 7.24-7.14 (m, 1H), 7.13 (td, J = 7.7, 1.1 Hz, 1H), 6.32 (s, 44%) and 6.27 (s, 56%) (1H), 5.19 (d, J = 16.1 Hz, 44%) and 5.18 (d, J = 17.0 Hz, 56%) (1H), 5.00 (d, J = 16.1 Hz, 56%) and 4.77 (d, J = 17.1 Hz, 44%) (1H), 4.35-3.90 (m, 6H), 3.70-3.58 (m, 1H), 3.45-3.22 (m, 2H), 2.79-2.28 (m, 9H), 1.89-1.41 (m, 4H), 1.26 (d, J = 6.7 Hz, 44%) and 1.23 (d, J = 6.7 Hz, 56%) (3H). |

TABLE I-continued

| Ex | Structure | Name | NMR |
|---|---|---|---|
| 37 | 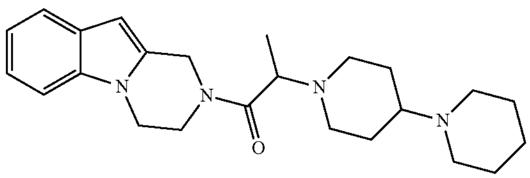 [SMILES: CC(C(=O)N1CCn2c(cc3ccccc32)C1)N1CCC(N2CCCCC2)CC1] | 2-(1,4'-bipiperidin-1'-yl)-1-(3,4-dihydro-pyrazino[1,2-a]indol-2(1H)-yl)propan-1-one | ¹H NMR (CDCl₃) δ: 7.57 (d, J = 7.8 Hz, 44%) and 7.53 (d, J = 7.6 Hz, 56%) (1H), 7.30 (d, J = 8.0 Hz, 1H), 7.29 (d, J = 8.0 Hz, 1H), 7.19 (m, 1H), 7.16-7.06 (m, 1H), 6.32 (s, 44%) and 6.27 (s, 56%) (1H), 5.20 (d, J = 16.1 Hz, 44%) and 5.17 (d, J = 17.1 Hz, 56%) (1H), 4.94 (d, J = 16.2 Hz, 56%) and 4.76 (d, J = 17.3 Hz, 44%) (1H), 4.37-3.78 (m, 4H), 3.62 (qd, J = 6.7, 1.9 Hz, 1H), 2.90-2.24 (m, 8H), 2.24-2.04 (m, 1H), 2.02-1.51 (m, 8H), 1.50-1.31 (m, 2H), 1.22 (d, J = 6.7 Hz, 44%) and 1.18 (d, J = 6.7 Hz, 56%) (3H). |
| 38 | 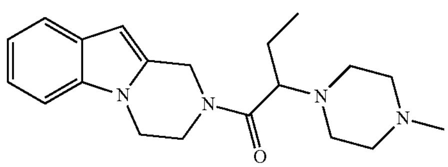 [SMILES: CCC(C(=O)N1CCn2c(cc3ccccc32)C1)N1CCN(C)CC1] | 1-(3,4-dihydro-pyrazino[1,2-a]indol-2(1H)-yl)-2-(4-methyl-piperazin-1-yl)butan-1-one | ¹H NMR (CDCl₃) δ: 7.58 (d, J = 7.8 Hz, 1H), 7.30 (d, J = 8.1 Hz, 1H), 7.20 (t, J = 7.5 Hz, 1H), 7.13 (t, J = 7.3 Hz, 1H), 6.33 (s, 45%) and 6.29 (s, 55%) (1H), 5.23-4.72 (m, 2H), 4.31-3.96 (m, 4H), 3.32 (dt, J = 9.4, 4.3 Hz, 1H), 2.79-2.63 (m, 2H), 2.63-2.50 (m, 2H), 2.50-2.14 (m, 4H), 2.29 (s, 45%) and 2.23 (s, 55%) (3H), 1.89-1.55 (m, 2H), 0.96-0.78 (m, 3H). |
| 39 | 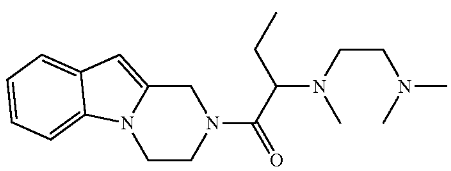 [SMILES: CCC(C(=O)N1CCn2c(cc3ccccc32)C1)N(C)CCN(C)C] | 1-(3,4-dihydro-pyrazino[1,2-a]indol-2(1H)-yl)-2-((2-(dimethyl-amino)ethyl)(methyl)amino)butan-1-one | ¹H NMR (CDCl₃) δ: 7.57 (d, J = 8.2 Hz, 1H), 7.29 (d, J = 8.3 Hz, 1H), 7.18 (t, J = 7.6 Hz, 1H), 7.11 (t, J = 7.4 Hz, 1H), 6.31 (s, 1H), 5.21 (d, J = 16.4 Hz, 50%) and 5.13 (d, J = 16.8 Hz, 50%) (1H), 5.03 (d, J = 16.3 Hz, 50%) and 4.83 (d, J = 16.9 Hz, 50%) (1H), 4.45-3.91 (m, 4H), 3.59-3.44 (m, 1H), 2.55-2.23 (m, 2H), 2.30 (s, 6H), 2.27 (s, 3H), 1.98-1.76 (m, 1H), 1.70-1.49 (m, 1H), 0.95-0.74 (m, 3H). |
| 40 | 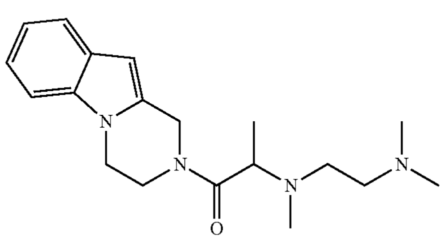 [SMILES: CC(C(=O)N1CCn2c(cc3ccccc32)C1)N(C)CCN(C)C] | 1-(3,4-dihydro-pyrazino[1,2-a]indol-2(1H)-yl)-2-((2-(dimethyl-amino)ethyl)(methyl)amino)propan-1-one | ¹H NMR (CDCl₃) δ: 7.57 (d, J = 7.3 Hz, 1H), 7.29 (d, J = 8.4 Hz, 1H), 7.18 (t, J = 7.4 Hz, 1H), 7.11 (t, J = 7.3 Hz, 1H), 6.31 (s, 50%) and 6.28 (s, 50%) (1H), 5.26 (d, J = 16.5 Hz, 50%) and 5.18 (d, J = 16.9 Hz, 1H), 5.12 (d, J = 16.3 Hz, 50%) and 4.75 (d, J = 16.9 Hz, 50%) (1H), 4.54-3.87 (m, 4H), 3.79 (dq, J = 9.6, 6.6 Hz, 1H), 2.75-1.89 (m, 4H), 2.24 (s, 3H), 2.23 (s, 6H), 1.19 (d, J = 6.7 Hz, 50%) and 1.17 (d, J = 6.5 Hz, 50%) (3H). |
| 41 | 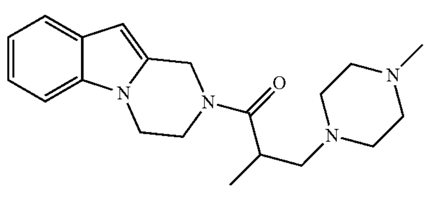 [SMILES: CC(CN1CCN(C)CC1)C(=O)N1CCn2c(cc3ccccc32)C1] | 1-(3,4-dihydro-pyrazino[1,2-a]indol-2(1H)-yl)-2-methyl-3-(4-methyl-piperazin-1-yl)propan-1-one | ¹H NMR (CD₃OD) δ: 7.49 (d, J = 7.8 Hz, 1H), 7.34 (d, J = 8.1 Hz, 1H), 7.13 (t, J = 7.6 Hz, 1H), 7.04 (t, J = 7.4 Hz, 1H), 6.29 (s, 1H), 5.25 (d, J = 16.4 Hz, 58%) and 5.08 (d, J = 16.4 Hz, 42%) (1H), 4.94 (d, J = 16.5 Hz, 58%) and 4.80 (d, J = 16.5 Hz, 42%) (1H), 4.56-3.75 (m, 4H), 3.70-3.45 (m, 1H), 2.91-1.73 (m, 10H), 2.13 (s, 42%) and 1.88 (s, 58%) (3H), 1.11 (d, J = 6.5 Hz, 42%), 1.07 (d, J = 6.8 Hz, 58%) (3H). |
| 42 | 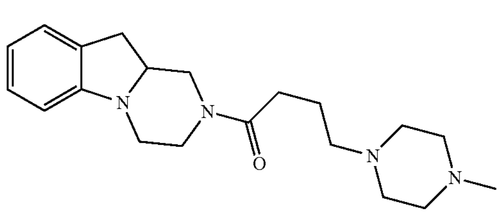 [SMILES: CN1CCN(CCCC(=O)N2CCN3c4ccccc4CC3C2)CC1] | 4-(4-methyl-piperazin-1-yl)-1-(3,4,10,10a-tetrahydro-pyrazino[1,2-a]indol-2(1H)- | ¹H NMR (CDCl₃) δ: 7.15-6.96 (m, 2H), 6.70 (t, J = 7.4 Hz, 1H), 6.48 (t, J = 6.9 Hz, 1H), 4.67 (dd, J = 24.1, 12.5 Hz, 1H), 3.98-3.73 (m, 1H), 3.70-3.51 (m, 1H), 3.50-3.33 (m, 1H), 3.32-3.08 (m, 1H), 3.08-2.95 (m, 1H), 2.95-2.72 (m, 2H), 2.70-2.37 (m, 13H), 2.32 (s, 3H), 1.87 (h, J = 7.3 Hz, 2H). |

TABLE I-continued

| Ex | Structure | Name | NMR |
|---|---|---|---|
| | | yl)butan-1-one | |
| 43 | 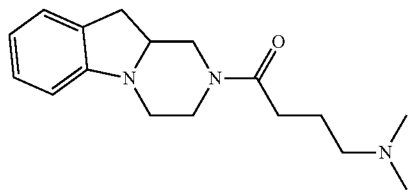 [SMILES: CN(C)CCCC(=O)N1CCN2c3ccccc3CC2C1] | 4-(dimethylamino)-1-(3,4,10,10a-tetrahydropyrazino[1,2-a]indol-2(1H)-yl)butan-1-one | ¹H NMR (CDCl₃) δ: 7.19-7.02 (m, 2H), 6.70 (t, J = 7.4 Hz, 1H), 6.48 (t, J = 6.7 Hz, 1H), 4.68 (dd, J = 23.4, 12.2 Hz, 1H), 4.02-3.78 (m, 1H), 3.66-3.51 (m, 1H), 3.51-3.33 (m, 1H), 3.31-3.08 (m, 1H), 3.06-2.72 (m, 3H), 2.71-2.33 (m, 5H), 2.27 (s, 6H), 1.86 (h, J = 7.2 Hz, 1H). |
| 44 | 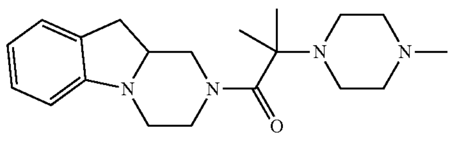 [SMILES: CN1CCN(C(C)(C)C(=O)N2CCN3c4ccccc4CC3C2)CC1] | 2-methyl-2-(4-methyl-piperazin-1-yl)-1-(3,4,10,10a-tetrahydropyrazino[1,2-a]indol-2(1H)-yl)propan-1-one | ¹H NMR (CD₃OD) δ: 7.18-6.95 (m, 2H), 6.66 (td, J = 7.4, 2.1 Hz, 1H), 6.55 (d, J = 7.9 Hz, 1H), 4.70-4.44 (m, 1H), 4.21-4.00 (m, 1H), 3.83-3.60 (m, 1H), 3.60-3.10 (m, 3H), 3.09-2.42 (m, 13H), 2.42-2.21 (m, 4H), 1.08 (dd, J = 19.5, 6.7 Hz, 3H). |
| 45 | 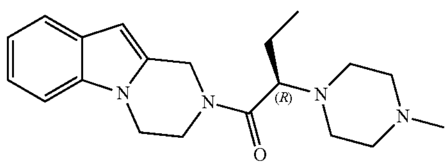 | (R)-1-(3,4-dihydropyrazino[1,2-a]indol-2(1H)-yl)-2-(4-methyl-piperazin-1-yl)butan-1-one | ¹H NMR (CDCl₃) δ: 7.58 (d, J = 7.8 Hz, 1H), 7.30 (d, J = 8.1 Hz, 1H), 7.20 (t, J = 7.5 Hz, 1H), 7.13 (t, J = 7.3 Hz, 1H), 6.33 (s, 45%) and 6.29 (s, 55%) (1H), 5.23-4.72 (m, 2H), 4.31-3.96 (m, 4H), 3.32 (dt, J = 9.4, 4.3 Hz, 1H), 2.79-2.63 (m, 2H), 2.63-2.50 (m, 2H), 2.50-2.14 (m, 4H), 2.29 (s, 45%) and 2.23 (s, 55%) (3H), 1.89-1.55 (m, 2H), 0.96-0.78 (m, 3H). |
| 46 | 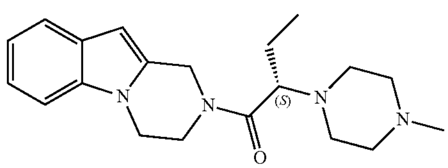 | (S)-1-(3,4-dihydropyrazino[1,2-a]indol-2(1H)-yl)-2-(4-methyl-piperazin-1-yl)butan-1-one | ¹H NMR (CDCl₃) δ: 7.58 (d, J = 7.8 Hz, 1H), 7.30 (d, J = 8.1 Hz, 1H), 7.20 (t, J = 7.5 Hz, 1H), 7.13 (t, J = 7.3 Hz, 1H), 6.33 (s, 45%) and 6.29 (s, 55%) (1H), 5.23-4.72 (m, 2H), 4.31-3.96 (m, 4H), 3.32 (dt, J = 9.4, 4.3 Hz, 1H), 2.79-2.63 (m, 2H), 2.63-2.50 (m, 2H), 2.50-2.14 (m, 4H), 2.29 (s, 45%) and 2.23 (s, 55%) (3H), 1.89-1.55 (m, 2H), 0.96-0.78 (m, 3H). |
| 47 | 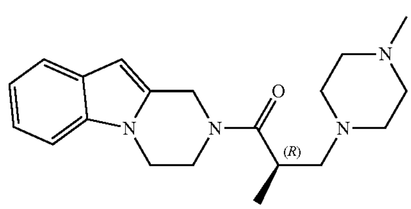 | (R)-1-(3,4-dihydropyrazino[1,2-a]indol-2(1H)-yl)-2-methyl-3-(4-methyl-piperazin-1-yl)propan-1-one | ¹H NMR (CD₃OD) δ: 7.49 (d, J = 7.8 Hz, 1H), 7.34 (d, J = 8.1 Hz, 1H), 7.13 (t, J = 7.6 Hz, 1H), 7.04 (t, J = 7.4 Hz, 1H), 6.29 (s, 1H), 5.25 (d, J = 16.4 Hz, 58%) and 5.08 (d, J = 16.4 Hz, 42%) (1H), 4.94 (d, J = 16.5 Hz, 58%) and 4.80 (d, J = 16.5 Hz, 42%) (1H), 4.56-3.75 (m, 4H), 3.70-3.45 (m, 1H), 2.91-1.73 (m, 10H), 2.13 (s, 42%) and 1.88 (s, 58%) (3H), 1.11 (d, J = 6.5 Hz, 42%), 1.07 (d, J = 6.8 Hz, 58%) (3H). |
| 48 | 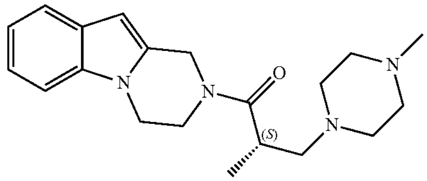 | (S)-1-(3,4-dihydropyrazino[1,2-a]indol-2(1H)-yl)-2-methyl-3-(4-methyl-piperazin-1-yl)propan-1-one | ¹H NMR (CD₃OD) δ: 7.49 (d, J = 7.8 Hz, 1H), 7.34 (d, J = 8.1 Hz, 1H), 7.13 (t, J = 7.6 Hz, 1H), 7.04 (t, J = 7.4 Hz, 1H), 6.29 (s, 1H), 5.25 (d, J = 16.4 Hz, 58%) and 5.08 (d, J = 16.4 Hz, 42%) (1H), 4.94 (d, J = 16.5 Hz, 58%) and 4.80 (d, J = 16.5 Hz, 42%) (1H), 4.56-3.75 (m, 4H), 3.70-3.45 (m, 1H), 2.91-1.73 (m, 10H), 2.13 (s, 42%) and 1.88 (s, 58%) (3H), 1.11 (d, J = 6.5 Hz, 42%), 1.07 (d, J = 6.8 Hz, 58%) (3H). |

TABLE I-continued

| Ex | Structure | Name | NMR |
|---|---|---|---|
| 49 | 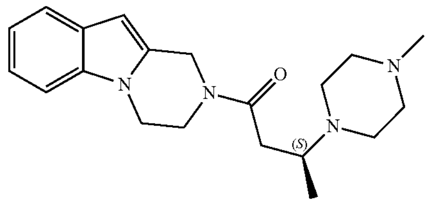 | (S)-1-(3,4-dihydro-pyrazino[1,2-a]indol-2(1H)-yl)-3-(4-methyl-piperazin-1-yl)butan-1-one | $^1$H NMR (CDCl$_3$) δ: 7.57 (d, J = 7.5 Hz, 1H), 7.29 (d, J = 8.6 Hz, 1H), 7.19 (t, J = 7.6 Hz, 1H), 7.12 (td, J = 7.4, 1.3 Hz, 1H), 6.30 (s, 1H), 4.97 (s, 35%) and 4.91 (s, 65%) (2H), 4.24-3.94 (m, 4H), 3.36-3.12 (m, 1H), 2.86-2.15 (m, 13H), 1.13 (d, J = 6.9 Hz, 35%) and 1.09 (d, J = 6.4 Hz, 65%) (3H). |
| 50 | 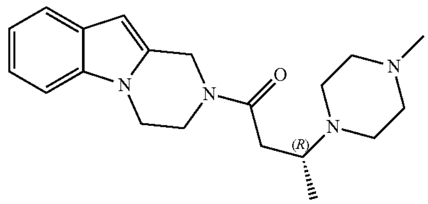 | (R)-1-(3,4-dihydro-pyrazino[1,2-a]indol-2(1H)-yl)-3-(4-methyl-piperazin-1-yl)butan-1-one | $^1$H NMR (CDCl$_3$) δ: 7.57 (d, J = 7.5 Hz, 1H), 7.29 (d, J = 8.6 Hz, 1H), 7.19 (t, J = 7.6 Hz, 1H), 7.12 (td, J = 7.4, 1.3 Hz, 1H), 6.30 (s, 1H), 4.97 (s, 35%) and 4.91 (s, 65%) (2H), 4.24-3.94 (m, 4H), 3.36-3.12 (m, 1H), 2.86-2.15 (m, 13H), 1.13 (d, J = 6.9 Hz, 35%) and 1.09 (d, J = 6.4 Hz, 65%) (3H). |
| 51 | 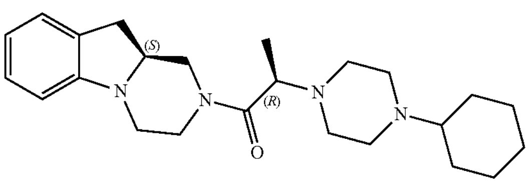 | (R)-2-(4-cyclohexyl-piperazin-1-yl)-1-((S)-3,4,10,10a-tetrahydro-pyrazino[1,2-a]indol-2(1H)-yl)propan-1-one | $^1$H NMR (CD$_3$OD) δ: 7.14-6.96 (m, 2H), 6.66 (t, J = 7.4 Hz, 1H), 6.54 (dd, J = 7.8, 2.9 Hz, 1H), 4.63-4.47 (m, 1H), 4.31 (d, J = 13.8 Hz, 40%) and 4.23 (d, J = 12.4 Hz, 60%) (1H), 3.79-3.43 (m, 3H), 3.28-3.18 (m, 1H), 3.16-2.68 (m, 4H), 2.67-2.49 (m, 8H), 2.37-2.13 (m, 1H), 2.03-1.86 (m, 2H), 1.86-1.72 (m, 2H), 1.69-1.52 (m, 1H), 1.38-0.96 (m, 8H). |
| 52 | 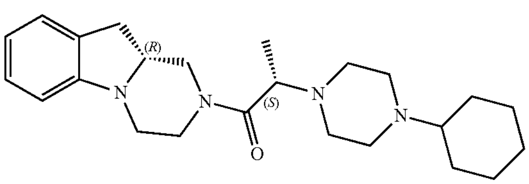 | (S)-2-(4-cyclohexyl-piperazin-1-yl)-1-((R)-3,4,10,10a-tetrahydro-pyrazino[1,2-a]indol-2(1H)-yl)propan-1-one | $^1$H NMR (CD$_3$OD) δ: 7.14-6.96 (m, 2H), 6.66 (t, J = 7.4 Hz, 1H), 6.54 (dd, J = 7.8, 2.9 Hz, 1H), 4.63-4.47 (m, 1H), 4.31 (d, J = 13.8 Hz, 40%) and 4.23 (d, J = 12.4 Hz, 60%) (1H), 3.79-3.43 (m, 3H), 3.28-3.18 (m, 1H), 3.16-2.68 (m, 4H), 2.67-2.49 (m, 8H), 2.37-2.13 (m, 1H), 2.03-1.86 (m, 2H), 1.86-1.72 (m, 2H), 1.69-1.52 (m, 1H), 1.38-0.96 (m, 8H). |
| 53 | 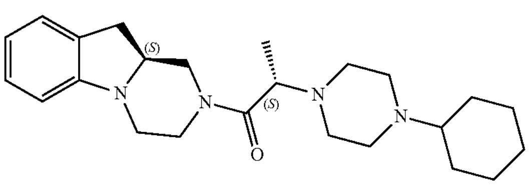 | (S)-2-(4-cyclohexyl-piperazin-1-yl)-1-((S)-3,4,10,10a-tetrahydro-pyrazino[1,2-a]indol-2(1H)-yl)propan-1-one | $^1$H NMR (CD$_3$OD) δ: 7.15-6.96 (m, 2H), 6.66 (t, J = 7.5 Hz, 1H), 6.55 (d, J = 7.8 Hz, 1H), 4.65-4.45 (m, 1H), 4.34 (d, J = 12.6 Hz, 37%) and 4.22 (d, J = 12.7 Hz, 63%) (1H), 3.79-3.55 (m, 2H), 3.48-2.74 (m, 5H), 2.74-2.46 (m, 9H), 2.33-2.10 (m, 1H), 2.01-1.86 (m, 2H), 1.86-1.75 (m, 2H), 1.70-1.57 (m, 1H), 1.40-0.97 (m, 8H). |
| 54 | 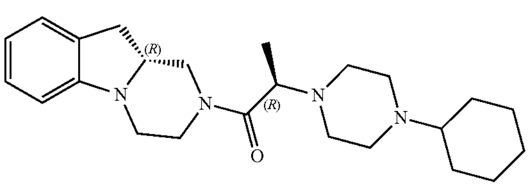 | (R)-2-(4-cyclohexyl-piperazin-1-yl)-1-((R)-3,4,10,10a-tetrahydro-pyrazino[1,2-a]indol-2(1H)-yl)propan-1-one | $^1$H NMR (CD$_3$OD) δ: 7.15-6.96 (m, 2H), 6.66 (t, J = 7.5 Hz, 1H), 6.55 (d, J = 7.8 Hz, 1H), 4.65-4.45 (m, 1H), 4.34 (d, J = 12.6 Hz, 37%) and 4.22 (d, J = 12.7 Hz, 63%) (1H), 3.79-3.55 (m, 2H), 3.48-2.74 (m, 5H), 2.74-2.46 (m, 9H), 2.33-2.10 (m, 1H), 2.01-1.86 (m, 2H), 1.86-1.75 (m, 2H), 1.70-1.57 (m, 1H), 1.40-0.97 (m, 8H). |
| 55 | HCl | 1-(3,4-dihydro-pyrazino[1,2-a]indol-2(1H)-yl)-2-morpholino-ethanone hydrochloride | $^1$H NMR (DMSO) δ: 10.27 (bs, 1H), 7.57-7.48 (m, 1H), 7.44 (d, J = 5.0 Hz, 62%) and 7.42 (d, J = 5.0 Hz, 38%) (1H), 7.13 (t, J = 7.5 Hz, 1H), 7.05 (t, J = 7.4 Hz, 1H), 6.36 (s, 62%) and 6.34 (s, 38%) (1H), 4.93 (s, 62%) and 4.89 (s, 38%) (2H), 4.68-4.35 (m, 2H), 4.26 (t, J = 5.4 Hz, 2H), 4.15 (t, J = 5.5 Hz, 1H), 4.05 (t, J = 4.9 Hz, |

TABLE I-continued

| Ex | Structure | Name | NMR |
|---|---|---|---|
| | | | 1H), 4.02-3.69 (m, 6H), 3.53-3.03 (m, 2H). |
| 56 | 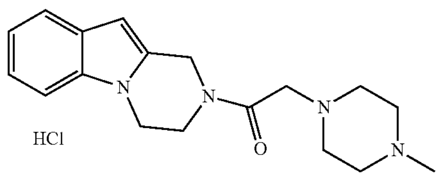 [SMILES: CN1CCN(CC(=O)N2CCn3c(cc4ccccc43)C2)CC1 ; Cl] | 1-(3,4-dihydro-pyrazino[1,2-a]indol-2(1H)-yl)-2-(4-methyl-piperazin-1-yl)ethanone hydrochloride | $^1$H NMR (DMSO) δ: 11.67 (bs, 1H), 7.58-7.46 (m, 1H), 7.43 (d, J = 8.0 Hz, 63%) and 7.42 (d, J = 8.1 Hz, 37%) (1H), 7.18-7.06 (m, 1H), 7.04 (t J = 7.4 Hz, 1H), 6.34 (s, 63%) and 6.33 (s, 37%) (1H), 4.91 (s, 2H), 4.51-4.08 (m, 4H), 4.07-3.92 (m, 2H), 3.59-3.23 (m, 8H), 2.80 (s, 3H). |
| 57 | 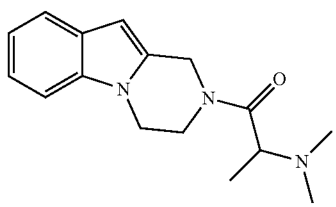 [SMILES: CC(C(=O)N1CCn2c(cc3ccccc32)C1)N(C)C] | 1-(3,4-dihydro-pyrazino[1,2-a]indol-2(1H)-yl)-2-(dimethyl-amino)propan-1-one | $^1$H NMR (CDCl$_3$) δ: 7.58 (d, J = 7.5 Hz, 1H), 7.34-7.25 (m, 1H), 7.25-7.13 (m, 1H), 7.12 (t, J = 7.3 Hz, 1H), 6.32 (s, 50%) and 6.30 (s, 50%) (1H), 5.26-5.12 (m, 1H), 5.08 (d, J = 16.3 Hz, 50%) and 4.81 (d, J = 17.0 Hz, 50%) (1H), 4.41-3.94 (m, 4H), 3.53 (dq, J = 16.2, 6.6 Hz, 1H), 2.25 (s, 6H), 1.21 (d, J = 6.8 Hz, 50%) and 1.20 (d, J = 6.6 Hz, 50%) (3H). |
| 58 | 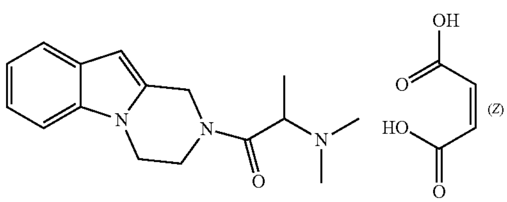 | 1-(3,4-dihydro-pyrazino[1,2-a]indol-2(1H)-yl)-2-(dimethyl-amino)propan-1-one maleate | $^1$H NMR (DMSO) δ: 9.68 (bs, 1H), 7.58-7.45 (m, 1H), 7.47-7.33 (m, 1H), 7.11 (t, J = 7.5 Hz, 1H), 7.09-6.95 (m, 1H), 6.34 (s, 56%) and 6.32 (s, 44%) (1H), 6.01 (s, 2H), 5.16-4.97 (m, 1H), 4.93 (d, J = 16.3 Hz, 44%) and 4.83 (d, J = 16.8 Hz, 56%) (1H), 4.66-4.48 (m, 1H), 4.34-3.82 (m, 4H), 2.72 (s, 6H), 1.41 (d, J = 6.8 Hz, 56%) and 1.37 (d, J = 6.8 Hz, 44%) (3H). |
| 59 | 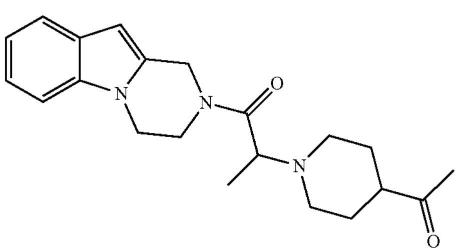 [SMILES: CC(=O)C1CCN(C(C)C(=O)N2CCn3c(cc4ccccc43)C2)CC1] | 2-(4-acetylpiper-azin-1-yl)-1-(3,4-dihydro-pyrazino[1,2-a]indol-2(1H)-yl)propan-1-one | $^1$H NMR (CDCl$_3$) δ: 7.58 (d, J = 7.7 Hz, 1H), 7.29 (d, J = 8.0 Hz, 57%) and 7.28 (d, J = 8.6 Hz, 43%) (1H), 7.20 (td, J = 7.5, 2.9 Hz, 1H), 7.13 (t, J = 7.4 Hz, 1H), 6.33 (s, 43%) and 6.29 (s, 57%) (1H), 5.21 (d, J = 16.0 Hz, 57%) and 5.18 (d, J = 17.1 Hz, 43%) (1H), 5.03 (d, J = 16.0 Hz, 57%) and 4.79 (d, J = 16.9 Hz, 43%) (1H), 4.32-3.93 (m, 4H), 3.85-3.12 (m, 5H), 2.71-2.37 (m, 4H), 2.07 (s, 43%) and 2.03 (s, 57%) (3H), 1.25 (d, J = 6.4 Hz, 43%) and 1.23 (d, J = 6.3 Hz, 57%) (3H). |
| 60 | 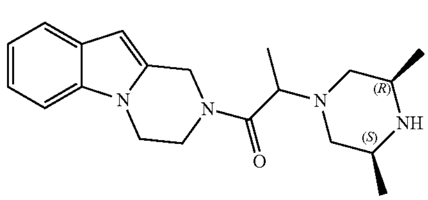 | 1-(3,4-dihydro-pyrazino[1,2-a]indol-2(1H)-yl)-2-((3S,5R)-3,5-dimethyl-piperazin-1-yl)propan-1-one | $^1$H NMR (CDCl$_3$) δ: 7.57 (dd, J = 7.7, 2.3 Hz, 1H), 7.29 (d, J = 8.2 Hz, 50%) and 7.28 (d, J = 7.7 Hz, 50%) (1H), 7.19 (tt, J = 8.4, 1.3 Hz, 1H), 7.17-7.08 (m, 1H), 6.33 (s, 50%) and 6.28 (s, 50%) (1H), 5.24 (d, J = 17.1 Hz, 50%) and 5.21 (d, J = 16.2 Hz, 50%) (1H), 5.01 (d, J = 16.3 Hz, 50%) and 4.73 (d, J = 16.9 Hz, 50%) (1H), 4.36-3.86 (m, 4H), 3.63 (q, J = 6.7 Hz, 50%) and 3.59 (q, J = 6.7 Hz, 50%) (1H), 3.04-2.41 (m, 4H), 2.24-2.06 (m, 1H), 1.98-1.81 (m, 1H), 1.22 (d, J = 6.7 Hz, 50%) and 1.20 (d, J = 6.7 Hz, 50%) (3H), 1.10 (dd, J = 14.3, 6.3 Hz, 50%) and 1.05-0.96 (m, 50%) (3H). |

TABLE I-continued

| Ex | Structure | Name | NMR |
|---|---|---|---|
| 61 | 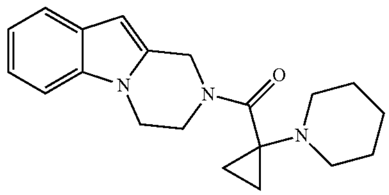 [SMILES: O=C(N1CCn2c(cc3ccccc32)C1)C1(N2CCCCC2)CC1] | (3,4-dihydro-pyrazino[1,2-a]indol-2(1H)-yl)(1-(piperidin-1-yl)cyclopropyl)methanone | $^1$H NMR (CDCl$_3$) δ: 7.58 (dd, J = 7.9, 0.8 Hz, 1H), 7.30 (d, J = 8.0 Hz, 1H), 7.24-7.15 (m, 1H), 7.17-7.08 (m, 1H), 6.30 (s, 1H), 5.05 (s, 2H), 4.28-4.06 (m, 4H), 2.47 (t, J = 5.2 Hz, 4H), 1.55-1.45 (m, 4H), 1.43-1.29 (m, 2H), 1.07-0.96 (m, 2H), 0.96-0.85 (m, 2H). |
| 62 | 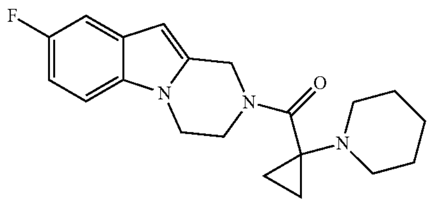 [SMILES: O=C(N1CCn2c(cc3cc(F)ccc32)C1)C1(N2CCCCC2)CC1] | (8-fluoro-3,4-dihydro-pyrazino[1,2-a]indol-2(1H)-yl)(1-(piperidin-1-yl)cyclopropyl)methanone | $^1$H NMR (CDCl$_3$) δ: 7.26-7.15 (m, 2H), 6.93 (td, J = 9.1, 2.5 Hz, 1H), 6.26 (s, 1H), 5.03 (s, 2H), 4.20-4.05 (m, 4H), 2.53-2.33 (m, 4H), 1.55-1.44 (m, 4H), 1.44-1.27 (m, 2H), 1.10-0.96 (m, 2H), 0.96-0.76 (m, 2H). |
| 63 | 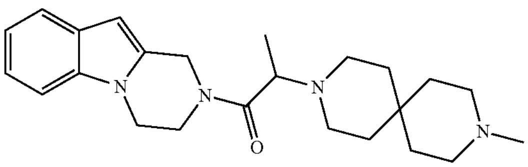 [SMILES: CC(C(=O)N1CCn2c(cc3ccccc32)C1)N1CCC2(CCN(C)CC2)CC1] | 1-(3,4-dihydro-pyrazino[1,2-a]indol-2(1H)-yl)-2-(9-methyl-3,9-diazaspiro[5.5]undecan-3-yl)propan-1-one | $^1$H NMR (CDCl$_3$) δ: 7.58 (d, J = 7.6 Hz, 50%) and 7.57 (d, J = 7.6 Hz, 50%) (1H), 7.29 (d, J = 8.0 Hz, 1H), 7.19 (t, J = 7.6 Hz, 1H), 7.12 (t, J = 7.1 Hz, 1H), 6.32 (s, 50%) and 6.28 (s, 50%) (1H), 5.24 (d, J = 16.0 Hz, 50%) and 5.18 (d, J = 17.1 Hz, 50%) (1H), 5.02 (d, J = 16.2 Hz, 50%) and 4.76 (d, J = 17.1 Hz, 50%) (1H), 4.33-3.93 (m, 4H), 3.60 (dq, J = 13.6, 6.8 Hz, 1H), 2.60-2.37 (m, 8H), 2.34 (s, 3H), 1.71 -1.27 (m, 8H), 1.24 (d, J = 6.7 Hz, 50%) and 1.21 (d, J = 6.7 Hz, 50%) (3H). |
| 64 | 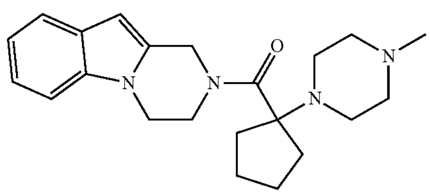 [SMILES: CN1CCN(C2(C(=O)N3CCn4c(cc5ccccc54)C3)CCCC2)CC1] | (3,4-dihydro-pyrazino[1,2-a]indol-2(1H)-yl)(1-(4-methyl-piperazin-1-yl)cyclopentyl)methanone | $^1$H NMR (DMSO) δ: 7.50 (d, J = 7.5 Hz, 1H), 7.37 (d, J = 7.6 Hz, 1H), 7.10 (t, J = 7.5 Hz, 1H), 7.06-6.97 (m, 1H), 6.31 (s, 1H), 5.41-4.76 (m, 2H), 4.50-3.89 (m, 4H), 3.06-2.21 (m, 11H), 2.17-1.71 (m, 4H), 1.65-1.33 (m, 4H). |
| 65 | 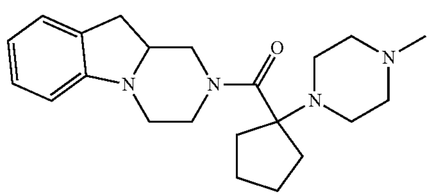 [SMILES: CN1CCN(C2(C(=O)N3CCN4c5ccccc5CC4C3)CCCC2)CC1] | (1-(4-methyl-piperazin-1-yl)cyclopentyl)(3,4,10,10a-tetrahydro-pyrazino[1,2-a]indol-2(1H)-yl)methanone | $^1$H NMR (CDCl$_3$) δ: 7.10 (t, J = 8.6 Hz, 2H), 6.70 (t, J = 7.5 Hz, 1H), 6.49 (d, J = 7.8 Hz, 1H), 5.14-4.45 (m, 2H), 3.75-3.51 (m, 1H), 3.51-3.26 (m, 1H), 3.23-2.19 (m, 13H), 2.47 (s, 3H), 2.17-1.28 (m, 8H). |
| 66 | 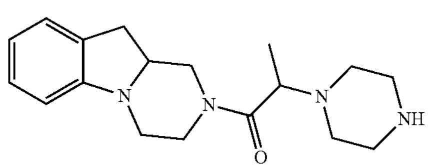 [SMILES: CC(C(=O)N1CCN2c3ccccc3CC2C1)N1CCNCC1] | 2-(piperazin-1-yl)-1-(3,4,10,10a-tetrahydro-pyrazino[1,2-a]indol-2(1H)-yl)propan-1-one | $^1$H NMR (CD$_3$OD) δ: 7.08 (d, J = 7.5 Hz, 1H), 7.04 (t, J = 7.5 Hz, 1H), 6.66 (t, J = 7.4 Hz, 1H), 6.55 (d, J = 7.8 Hz, 1H), 4.62-4.48 (m, 1H), 4.40-4.14 (m, 1H), 3.77-3.44 (m, 3H), 3.28-2.94 (m, 3H), 2.95-2.76 (m, 4H), 2.75-2.41 (m, 6H), 1.21 (d, J = 6.8 Hz, 38%) and 1.15 (dd, J = 7.0, 1.8 Hz, 62%) (3H). |
| 67 | 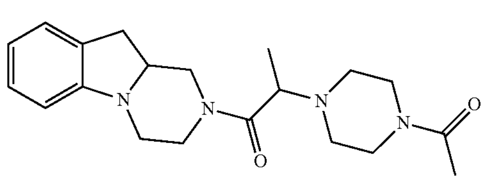 [SMILES: CC(=O)N1CCN(C(C)C(=O)N2CCN3c4ccccc4CC3C2)CC1] | 2-(4-acetyl-piperazin-1-yl)-1-(3,4,10,10a-tetrahydro-pyrazino[1,2- | $^1$H NMR (CDCl$_3$) δ: 7.17-7.01 (m, 2H), 6.71 (t, J = 7.4 Hz, 1H), 6.49 (t, J = 7.3 Hz, 1H), 4.81-4.56 (m, 1H), 4.32-4.00 (m, 1H), 3.88-3.28 (m, 7H), 3.27-2.73 (m, 4H), 2.72-2.32 (m, 5H), 2.08 (s, 3H), 1.46-1.03 (m, 3H). |

TABLE I-continued

| Ex | Structure | Name | NMR |
|---|---|---|---|
| 68 | 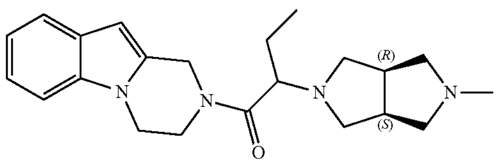 | 1-(3,4-dihydro-pyrazino[1,2-a]indol-2(1H)-yl)-2-((3aR,6aS)-5-methyl-hexahydro-pyrrolo[3,4-c]pyrrol-2(1H)-yl)butan-1-one ...a]indol-2(1H)-yl)propan-1-one | $^1$H NMR (CDCl$_3$) δ: 7.62-7.51 (m, 1H), 7.30 (d, J = 7.8 Hz, 1H), 7.19 (t, J = 7.7 Hz, 1H), 7.12 (td, J = 7.4, 1.3 Hz, 1H), 6.32 (s, 40%) and 6.28 (s, 60%) (1H), 5.36 (d, J = 16.2 Hz, 60%) and 5.06 (d, J = 17.1 Hz, 40%) (1H), 5.15 (d, J = 16.3 Hz, 60%) and 4.92 (d, J = 17.1 Hz, 40%) (1H), 4.36-4.02 (m, 4H), 3.40-3.24 (m, 1H), 2.90-2.58 (m, 5H), 2.57-2.18 (m, 4H), 2.32 (s, 40%) and 2.23 (s, 60%) (3H), 2.18-2.03 (m, 1H), 1.85-1.66 (m, 2H), 0.90 (t, J = 7.4 Hz, 40%) and 0.87 (t, J = 7.4 Hz, 60%) (3H). |

BIOLOGICAL ACTIVITY

Pharmacological Study
Human Sigma 1 Receptor Radioligand Assay

To investigate binding properties of sigma 1 receptor ligands to human sigma 1 receptor, transfected HEK-293 membranes and [$^3$H](+)-pentazocine (Perkin Elmer, NET-1056), as the radioligand, were used. The assay was carried out with 7 μg of membrane suspension, 5 nM of [$^3$H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM TrisHCL (pH7.4). Filters were dried and counted at approximately 40% efficiency in a MicroBeta scintillation counter (Perkin-Elmer) using EcoScint liquid scintillation cocktail.

Some of the results obtained are shown in table (II) below:

TABLE II

| Ex | Ki (nM) |
|---|---|
| 1 | 105 |
| 2 | 96.1 |
| 3 | 68.2 |
| 4 | 10.2 |
| 5 | 39.8 |
| 6 | 14.4 |
| 7 | 24.8 |
| 8 | 29.6 |
| 9 | 129 |
| 10 | 25 |
| 11 | 60.8 |
| 12 | 14.6 |
| 13 | 69.7 |
| 14 | 24 |
| 15 | 26.2 |
| 16 | 22.2 |
| 17 | 10.9 |
| 19 | 55.9 |
| 20 | 28.8 |
| 21 | 21.9 |
| 22 | 292 |
| 24 | 37.6 |
| 25 | 118 |
| 26 | 123 |
| 27 | 25.6 |
| 29 | 125 |
| 30 | 241 |
| 32 | 234 |
| 33 | 84.3 |
| 34 | 56.5 |
| 37 | 500 |
| 38 | 89.3 |
| 39 | 427 |
| 41 | 73 |
| 43 | 151 |
| 44 | 175 |
| 46 | 75.5 |
| 47 | 49.5 |
| 48 | 142 |
| 49 | 91.7 |
| 50 | 251 |
| 51 | 59.9 |
| 52 | 142.1 |
| 53 | 94.7 |
| 54 | 71.6 |

The invention claimed is:
1. A compound of formula (I), or a pharmaceutically acceptable salt, enantiomer, diastereomer or racemate thereof:

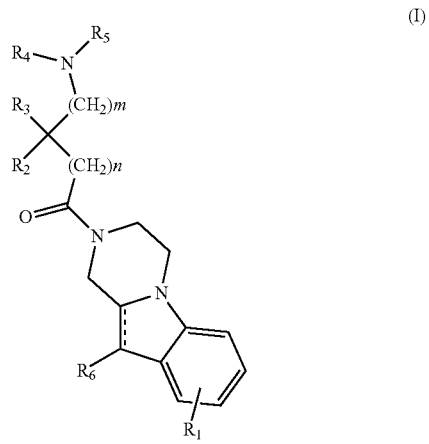

(I)

wherein m is selected from 0, 1, 2, 3 and 4;

n is selected from 0, 1, 2, 3 and 4;

==== represents a single or double bond;

$R_1$ represents one or more optional and independent substitutions in the benzene moiety selected from the group consisting of alkyl, cycloalkyl, cycloalkylalkyl, alkenyl, aryl, arylalkyl, heterocyclyl, heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_tR_8$, —$NR_8R_9$, —$NR_8C(O)R_9$, —$NO_2$, —$N=CR_8R_9$, and halogen;

$R_2$ and $R_3$ are independently selected from the group consisting of hydrogen, alkyl, cycloalkyl, cycloalkylalkyl, alkenyl, aryl, heterocyclyl, heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, and halogen;

or $R_2$ and $R_3$, together with the bridging carbon atom, form a cycloalkyl or a heterocyclyl;

$R_4$ and $R_5$ are independently selected from the group consisting of hydrogen, alkyl, cycloalkyl, cycloalkylalkyl, alkenyl, aryl, arylalkyl, heterocyclyl, heterocyclylalkyl, —$COR_8$, —$C(O)OR_8$, and —$C(O)NR_8R_9$;

or $R_4$ and $R_5$, together with the bridging nitrogen atom, form a heterocyclyl, wherein the heterocyclyl is not phthalimidyl;

$R_6$ is selected from the group consisting of hydrogen, alkyl, cycloalkyl, cycloalkylalkyl, alkenyl, aryl, arylalkyl, heterocyclyl, heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen;

t is selected from 0, 1 and 2; and $R_8$ and $R_9$ are each independently selected from hydrogen, alkyl, cycloalkyl, alkenyl, aryl, heterocyclyl and halogen;

wherein the aforementioned groups may be substituted at one or more available positions by one or more substituents selected from the group consisting of OR', =O, SR', SOR', $SO_2R'$, $OSO_2R'$, $OSO_3R'$, $NO_2$, NHR', $N(R')_2$, =N—R', N(R')COR', $N(COR')_2$, $N(R')SO_2R'$, N(R')C(=NR')N(R')R', $N_3$, CN, halogen, COR', COOR', OCOR', OCOOR', OCONHR', $OCON(R')_2$, CONHR', $CON(R')_2$, CON(R')OR', $CON(R')SO_2R'$, $PO(OR')_2$, PO(OR')R', PO(OR')(N(R')R'), $C_1$-$C_{12}$ alkyl, $C_3$-$C_{10}$ cycloalkyl, $C_2$-$C_{12}$ alkenyl, $C_2$-$C_{12}$ alkynyl, aryl and heterocyclyl, wherein each R' is independently selected from the group consisting of hydrogen, OH, $NO_2$, $NH_2$, SH, CN, halogen, COH, COalkyl, COOH, $C_1$-$C_{12}$ alkyl, $C_3$-$C_{10}$ cycloalkyl, $C_2$-$C_{12}$ alkenyl, $C_2$-$C_{12}$ alkynyl, aryl and heterocyclyl; and with the proviso that the compound of formula (I) does not represent:

3-(2-[(trifluoroacetamido)acetyl]-1,2,3,4-tetrahydropyrazino[1,2-a]indol-10-yl]-4-(1-methyl-3-indolyl)-1H-pyrrole-2,5-dione, 3-[2-(aminoacetyl)-1,2,3,4-tetrahydropyrazino[1,2-a]indol-10-yl]-4-(1-methyl-3-indolyl)-1H-pyrrole-2,5-dione hydrochloride, 8-chloro-2-(diethylaminoacetyl)-1,2,3,4-tetrahydro-10-phenylpyrazino[1,2-a]indole, 4-(dimethylamino)-1-(10-phenyl-3,4-dihydropyrazino[1,2-a]indol-2(1H)-yl)butan-1-one, or 3-morpholino-1-(10-phenyl-3,4-dihydropyrazino[1,2-a]indol-2(1H)-yl)propan-1-one.

2. The compound according to claim 1, wherein m is selected from 0, 1 and 2 and/or n is selected from 0, 1 and 2.

3. The compound according to claim 2, consisting of at least one condition selected from the group consisting of (a), (b), (c) and (d):

(a) in formula (I),
$R_1$ represents one or more optional and independent substitutions in the benzene moiety selected from the group consisting of alkyl and halogen;

(b) in formula (I),
$R_2$ and $R_3$ are independently selected from the group consisting of hydrogen, alkyl and cycloalkyl; or
$R_2$ and $R_3$, together with the bridging carbon atom, form a cycloalkyl or a heterocyclyl;

(c) in formula (I),
$R_4$ and $R_5$ are independently selected from the group consisting of hydrogen, alkyl and cycloalkyl; or
$R_4$ and $R_5$, together with the bridging nitrogen atom, form a heterocyclyl; and (d) in formula (I),
$R_6$ is selected from the group consisting of hydrogen and alkyl.

4. The compound according to claim 1, wherein $R_1$ represents one or more optional and independent substitutions in the benzene moiety selected from the group consisting of alkyl and halogen.

5. The compound according to claim 4, consisting of at least one condition selected from the group consisting of (a), (b), (c) and (d):

(a) in formula (I),
m is selected from 0, 1 and 2, and/or
n is selected from 0, 1 and 2;

(b) in formula (I),
R2 and R3 are independently selected from the group consisting of hydrogen, alkyl and cycloalkyl; or
R2 and R3, together with the bridging carbon atom, form a cycloalkyl or a heterocyclyl;

(c) in formula (I),
$R_4$ and $R_5$ are independently selected from the group consisting of hydrogen, alkyl and cycloalkyl; or
R4 and R5, together with the bridging nitrogen atom, form a heterocyclyl; and (d) in formula (I),
R6 is selected from the group consisting of hydrogen and alkyl.

6. The compound according to claim 1, wherein $R_2$ and $R_3$ are independently selected from the group consisting of hydrogen, alkyl and cycloalkyl; or $R_2$ and $R_3$, together with the bridging carbon atom, form a cycloalkyl or a heterocyclyl.

7. The compound according to claim 6, consisting of at least one condition selected from the group consisting of (a), (b), (c) and (d):

(a) in formula (I),
$R_1$ represents one or more optional and independent substitutions in the benzene moiety selected from the group consisting of alkyl and halogen;

(b) in formula (I),
m is selected from 0, 1 and 2, and/or
n is selected from 0, 1 and 2;

(c) in formula (I),
$R_4$ and $R_5$ are independently selected from the group consisting of hydrogen, alkyl and cycloalkyl; or
$R_4$ and $R_5$, together with the bridging nitrogen atom, form a heterocyclyl; and (d) in formula (I),
R$_6$ is selected from the group consisting of hydrogen and alkyl.

8. The compound according to claim 1, wherein R$_4$ and R$_5$ are independently selected from the group consisting of hydrogen, alkyl, and cycloalkyl; or R$_4$ and R$_5$, together with the bridging nitrogen atom, form a heterocyclyl.

9. The compound according to claim 8, consisting of at least one condition selected from the group consisting of (a), (b), (c) and (d):
(a) in formula (I),
R$_1$ represents one or more optional and independent substitutions in the benzene moiety selected from the group consisting of alkyl and halogen;
(b) in formula (I),
m is selected from 0, 1 and 2, and/or
n is selected from 0, 1 and 2;
(c) in formula (I),
R$_2$ and R$_3$ are independently selected from the group consisting of hydrogen, alkyl and cycloalkyl; or
R$_2$ and R$_3$, together with the bridging nitrogen atom, form a heterocyclyl; and
(d) in formula (I),
R$_6$ is selected from the group consisting of hydrogen and alkyl.

10. The compound according to claim 1, wherein R$_6$ is selected from the group consisting of hydrogen and alkyl.

11. The compound according to claim 10, consisting of at least one condition selected from the group consisting of (a), (b), (c) and (d):
(a) in formula (I),
R$_1$ represents one or more optional and independent substitutions in the benzene moiety selected from the group consisting of alkyl and halogen;
(b) in formula (I),
m is selected from 0, 1 and 2, and/or
n is selected from 0, 1 and 2;
(c) in formula (I),
R$_2$ and R$_3$ are independently selected from the group consisting of hydrogen, alkyl and cycloalkyl; or
R$_2$ and R$_3$, together with the bridging carbon atom, form a cycloalkyl or a heterocyclyl; and
(d) in formula (I),
R$_4$ and R$_5$ are independently selected from the group consisting of hydrogen, alkyl and cycloalkyl; or
R$_4$ and R$_5$, together with the bridging nitrogen atom, form a heterocyclyl.

12. A pharmaceutical composition comprising at least one compound of formula (I) according to claim 1, or a pharmaceutically acceptable salt, enantiomer, diastereomer or racemate thereof, and a pharmaceutically acceptable excipient.

13. A method for modulating sigma receptor activity in a subject, the method comprising administering to the subject a therapeutically effective amount of the compound of formula (I) according to claim 1, or a pharmaceutically acceptable salt, enantiomer, diastereomer or racemate thereof.

14. The method according to claim 13, wherein the subject suffers from a disease or condition selected from the group consisting of pain, diarrhea, hyperlipidemia, hypertriglyceridemia, hypercholesterolemia, obesity, migraine, arthritis, hypertension, arrhythmia, ulcer, glaucoma, tardive dyskinesia, stroke, epilepsy, stress, cancer, a learning deficit, a memory deficit, an attention deficit, an addiction to a drug, an addiction to a chemical substance, an inflammation disease, an autoimmune disease, a cognition disorder, a lipoprotein disorder, a neurodegenerative disease, a demyelinating disease and a psychotic condition.

15. The method according to claim 14, wherein the pain is selected from the group consisting of neuropathic pain, inflammatory pain and a pain condition involving allodynia and/or hyperalgesia.

16. The method according to claim 14, wherein the addiction is to a drug or chemical substance selected from the group consisting of cocaine, amphetamine, ethanol and nicotine.

17. The method according to claim 14, wherein the stroke is ischemic stroke.

18. The method according to claim 14, wherein the psychotic condition is selected from the group consisting of depression, anxiety and schizophrenia.

19. A process for the preparation of a compound of formula (I) according to claim 1, or a pharmaceutically acceptable salt, enantiomer, diastereomer or racemate thereof, the process being selected from:
a) a process comprising the reaction between a compound of formula (II)

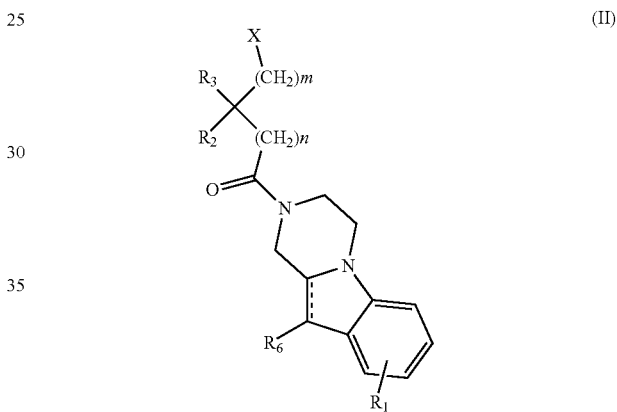

wherein X is halogen, methylsulfonyl, p-toluenesulfonyl, trifluoromethylsulfonyl, p-nitrophenyl or ethyltrifluoroacetate;
m is selected from 0, 1, 2, 3 and 4;
n is selected from 0, 1, 2, 3 and 4;
==== represents a single or double bond;
R$_1$ represents one or more optional and independent substitutions in the benzene moiety selected from the group consisting of alkyl, cycloalkyl, cycloalkylalkyl, alkenyl, aryl, aralkyl, heterocyclyl, heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_l$—R$_8$, —NR$_8$R$_9$, NR$_8$C(O)R$_9$, —NO$_2$, —N=CR$_8$R$_9$, and halogen;
R$_2$ and R$_3$ are independently selected from the group consisting of hydrogen, alkyl, cycloalkyl, cycloalkylalkyl, alkenyl, aryl, heterocyclyl, heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$-R$_8$, NR$_8$R$_9$, —NR$_8$C(O)R$_9$, and halogen:
or R$_2$ and R$_3$, together with the bridging carbon atom, form a cycloalkyl or a heterocyclyl;
R$_6$ is selected from the group consisting of hydrogen, alkyl, cycloalkyl, cycloalkylalkyl, alkenyl, aryl, arylalkyl, heterocyclyl, heterocyclylalkyl, —COR$_8$, —C(O)OR$_8$, —C(O)NR$_8$R$_9$, —CH=NR$_8$, —CN, —OR$_8$, —OC(O)R$_8$, —NR$_8$R$_9$, —NR$_8$C(O)R$_9$, —NO$_2$, —N=CR$_8$R$_9$, and halogen:

t is selected from 0, 1 and 2; and

R$_8$ and R$_9$ are each independently selected from hydrogen, alkyl, cycloalkyl, alkenyl, aryl, heterocyclyl and halogen;

with a compound of formula (III)

(III)

wherein R$_4$ and R$_5$ are independently selected from the group consisting of hydrogen, alkyl, cycloalkyl, cycloalkylalkyl, alkenyl, aryl, arylalkyl, heterocyclyl, heterocyclylalkyl, —COR$_8$, —C(O)OR$_8$, and —C(O)NR$_8$R$_9$;

or R$_4$ and R$_5$, together with the bridging nitrogen atom, form a heterocyclyl, wherein the heterocyclyl is not phthalimidyl; and R$_8$ and R$_9$ are each independently selected from hydrogen, alkyl, cycloalkyl, alkenyl, aryl, heterocyclyl and halogen; or b) a process comprising the reaction between a compound of formula (IV):

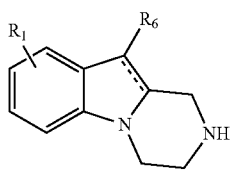

(IV)

wherein

═══ represents a single or double bond;

R$_1$ represents one or more optional and independent substitutions in the benzene moiety selected from the group consisting of alkyl, cycloalkyl, cycloalkylalkyl, alkenyl, aryl, arylalkyl, heterocyclyl, heterocyclylalkyl, —COR$_8$, C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, and halogen;

R$_6$ is selected from the group consisting of hydrogen, alkyl, cycloalkyl, cycloalkylalkyl, alkenyl, aryl, arylalkyl, heterocyclyl, heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_1$—R$_8$, —NR$_8$R$_9$, —NR$_8$C(0)R$_9$, —NO$_2$, —N=CR$_8$R$_9$, and halogen;

t is selected from 0, 1 and 2; and

R$_8$ and R$_9$ are each independently selected from hydrogen, alkyl, cycloalkyl, alkenyl, aryl, heterocyclyl and halogen;

with a compound of formula (VI):

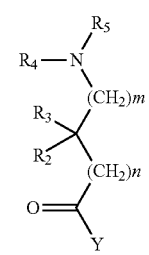

(VI)

wherein Y is OH, halogen, methylsulfonyl, p-toluenesulfonyl, trifluoromethylsulfonyl, p-nitrophenyl or ethyltrifluoroacetate;

m is selected from 0,1, 2, 3 and 4;

n is selected from 0, 1, 2, 3 and 4;

R$_2$ and R$_3$ are independently selected from the group consisting of hydrogen, alkyl, cycloalkyl, cycloalkylalkyl, alkenyl, aryl, heterocyclyl, heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, and halogen;

or R$_2$ and R$_3$, together with the bridging carbon atom, form a cycloalkyl or a heterocyclyl;

R$_4$ and R$_5$ are independently selected from the group consisting of hydrogen, alkyl, cycloalkyl, cycloalkylalkyl, alkenyl, aryl, arylalkyl, heterocyclyl, heterocyclylalkyl, —COR$_8$, —C(O)OR$_8$, and —C(O)NR$_8$R$_9$;

or R$_4$ and R$_5$, together with the bridging nitrogen atom, form a heterocyclyl, wherein the heterocyclyl is not phthalimidyl;

t is selected from 0, 1 and 2; and

R$_8$ and R$_9$ are each independently selected from hydrogen, alkyl, cycloalkyl, alkenyl, aryl heterocyclyl and halogen;

or c) a process comprising the reaction between a compound of formula (VII):

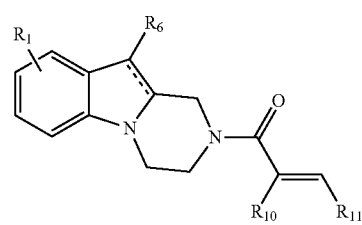

(VII)

wherein R$_{10}$ and R$_{11}$ are independently selected from the group consisting of hydrogen, alkyl, cycloalkyl, cycloalkylalkyl, alkenyl, aryl, arylalkyl, heterocyclyl, and heterocyclylalkyl;

═══ represents a single or double bond;

R$_1$ represents one or more optional and independent substitutions in the benzene moiety selected from the group consisting of alkyl, cycloalkyl, cycloalkylalkyl, alkenyl, aryl, arylalkyl, heterocyclyl, heterocyclylalkyl, —COR$_8$, —C(O)OR$_8$, —C(O)NR$_8$R$_9$, —CH=NR$_8$, —CN, —OR₈, —OC(O)R₈, —S(O)ₜ—R₈, —NR₈R₉, —NR₈C(O)R₉, —NO₂, —N=CR₈R₉, and halogen;

t is selected from 0, 1 and 2; and

R₈ and R₉ are each independently selected from hydrogen, alkyl, cycloalkyl, alkenyl, aryl, heterocyclyl and halogen;

with a compound of formula (III):

(III)

wherein R₄ and R₅ are independently selected from the group consisting of hydrogen, alkyl, cycloalkyl, cycloalkylalkyl, alkenyl, aryl, arylalkyl, heterocyclyl, heterocyclylalkyl, —COR₈, —C(O)OR₈, and —C(O)NR₈R₉;

or R₄ and R₅, together with the bridging nitrogen atom, form a heterocyclyl, wherein the heterocyclyl is not phthalimidyl; and R₈ and R₉ are each independently selected from hydrogen, alkyl, cycloalkyl, alkenyl, aryl, heterocyclyl and halogen;

and optionally reacting the compound of formula (I) with an acid or base to provide a pharmaceutically acceptable salt of the compound of formula (I).

20. A compound selected from the group consisting of:

1-(3,4-dihydropyrazino[1,2-a]indol-2(1H)-yl)-2-(4-methylpiperazin-1-yl)propan-1-one,
1-(3,4-dihydropyrazino[1,2-a]indol-2(1H)-yl)-2-methyl-2-(4-methylpiperazin-1-yl)propan-1-one,
1-(3,4-dihydropyrazino[1,2-a]indol-2(1H)-yl)-3-(4-methylpiperazin-1-yl)butan-1-one,
2-(azepan-1-yl)-1-(3,4-dihydropyrazino[1,2-a]indol-2(1H)-yl)ethanone hydrochloride,
1-(3,4-dihydropyrazino[1,2-a]indol-2(1H)-yl)-2-(piperidin-1-yl)ethanone hydrochloride,
2-(4-benzylpiperidin-1-yl)-1-(3,4-dihydropyrazino[1,2-a]indol-2(1H)-yl)ethanone hydrochloride,
2-(azepan-1-yl)-1-(3,4-dihydropyrazino[1,2-a]indol-2(1H)-yl)propan-1-one,
2-(azepan-1-yl)-1-(3,4-dihydropyrazino[1,2-a]indol-2(1H)-yl)propan-1-one maleate,
1-(3,4-dihydropyrazino[1,2-a]indol-2(1H)-yl)-2-(piperidin-1-yl)propan-1-one,
2-(4-benzylpiperidin-1-yl)-1-(3,4-dihydropyrazino[1,2-a]indol-2(1H)-yl)propan-1-one,
1-(3,4-dihydropyrazino[1,2-a]indol-2(1H)-yl)-4-(dimethylamino)butan-1-one,
2-(azepan-1-yl)-1-(8-fluoro-3,4-dihydropyrazino[1,2-a]indol-2(1H)-yl)ethanone,
2-(azepan-1-yl)-1-(8-methyl-3,4-dihydropyrazino[1,2-a]indol-2(1H)-yl)propan-1-one,
1-(10-methyl-3,4-dihydropyrazino[1,2-a]indol-2(1H)-yl)-2-(piperidin-1-yl)ethanone,
2-(4-benzylpiperidin-1-yl)-1-(10-methyl-3,4-dihydropyrazino[1,2-a]indol-2(1H)-yl)ethanone,
1-(8-fluoro-3,4-dihydropyrazino[1,2-a]indol-2(1H)-yl)-4-(piperidin-1-yl)butan-1-one,
3-(azepan-1-yl)-1-(3,4-dihydropyrazino[1,2-a]indol-2(1H)-yl)propan-1-one,
(R)-1-(3,4-dihydropyrazino[1,2-a]indol-2(1H)-yl)-2-(4-methylpiperazin-1-yl)propan-1-one,
(S)-1-(3,4-dihydropyrazino[1,2-a]indol-2(1H)-yl)-2-(4-methylpiperazin-1-yl)propan-1-one,
1-(3,4-dihydropyrazino[1,2-a]indol-2(1H)-yl)-4-(piperidin-1-yl)butan-1-one,
4-(azepan-1-yl)-1-(8-fluoro-3,4-dihydropyrazino[1,2-a]indol-2(1H)-yl)butan-1-one,
1-(3,4-dihydropyrazino[1,2-a]indol-2(1H)-yl)-4-(4-methylpiperazin-1-yl)butan-1-one,
1-(8-fluoro-3,4-dihydropyrazino[1,2-a]indol-2(1H)-yl)-4-(4-methylpiperazin-1-yl)butan-1-one,
2-(4-cyclohexylpiperazin-1-yl)-1-(3,4-dihydropyrazino[1,2-a]indol-2(1H)-yl)propan-1-one,
2-(4-methylpiperazin-1-yl)-1-(3,4,10,10a-tetrahydropyrazino[1,2-a]indol-2(1H)-yl)propan-1-one,
1-(8-fluoro-3,4-dihydropyrazino[1,2-a]indol-2(1H)-yl)-2-(4-methylpiperazin-1-yl)propan-1-one,
2-(4-cyclohexylpiperazin-1-yl)-1-(8-fluoro-3,4-dihydropyrazino[1,2-a]indol-2(1H)-yl)propan-1-one,
1-(8-fluoro-3,4-dihydropyrazino[1,2-a]indol-2(1H)-yl)-2-(4-methyl-1,4-diazepan-1-yl)propan-1-one,
2-(4-ethylpiperazin-1-yl)-1-(8-fluoro-3,4-dihydropyrazino[1,2-a]indol-2(1H)-yl)propan-1-one,
2-(2-(diethylamino)ethylamino)-1-(3,4-dihydropyrazino[1,2-a]indol-2(1H)-yl)propan-1-one,
1-(3,4-dihydropyrazino[1,2-a]indol-2(1H)-yl)-2-(1,4-oxazepan-4-yl)propan-1-one,
(R)-2-(4-methylpiperazin-1-yl)-1-((S)-3,4,10,10a-tetrahydropyrazino[1,2-a]indol-2(1H)-yl)propan-1-one,
(S)-2-(4-methylpiperazin-1-yl)-1-((R)-3,4,10,10a-tetrahydropyrazino[1,2-a]indol-2(1H)-yl)propan-1-one,
(S)-2-(4-methylpiperazin-1-yl)-1-((S)-3,4,10,10a-tetrahydropyrazino[1,2-a]indol-2(1H)-yl)propan-1-one,
(R)-2-(4-methylpiperazin-1-yl)-1-((R)-3,4,10,10a-tetrahydropyrazino[1,2-a]indol-2(1H)-yl)propan-1-one,
1-(3,4-dihydropyrazino[1,2-a]indol-2(1H)-yl)-2-(4-(tetrahydro-2H-pyran-4-yl)piperazin-1-yl)propan-1-one,
2-(1,4'-bipiperidin-1'-yl)-1-(3,4-dihydropyrazino[1,2-a]indol-2(1H)-yl)propan-1-one,
1-(3,4-dihydropyrazino[1,2-a]indol-2(1H)-yl)-2-(4-methylpiperazin-1-yl)butan-1-one,
1-(3,4-dihydropyrazino[1,2-a]indol-2(1H)-yl)-2-((2-(dimethylamino)ethyl)(methyl)amino)butan-1-one,
1-(3,4-dihydropyrazino[1,2-a]indol-2(1H)-yl)-2-((2-(dimethylamino)ethyl)(methyl)amino)propan-1-one,
1-(3,4-dihydropyrazino[1,2-a]indol-2(1H)-yl)-2-methyl-3-(4-methylpiperazin-1-yl)propan-1-one,
4-(4-methylpiperazin-1-yl)-1-(3,4,10,10a-tetrahydropyrazino[1,2-a]indol-2(1H)-yl)butan-1-one,
4-(dimethylamino)-1-(3,4,10,10a-tetrahydropyrazino[1,2-a]indol-2(1H)-yl)butan-1-one,
2-methyl-2-(4-methylpiperazin-1-yl)-1-(3,4,10,10a-tetrahydropyrazino[1,2-a]indol-2(1H)-yl)propan-1-one,
(R)-1-(3,4-dihydropyrazino[1,2-a]indol-2(1H)-yl)-2-(4-methylpiperazin-1-yl)butan-1-one,
(S)-1-(3,4-dihydropyrazino[1,2-a]indol-2(1H)-yl)-2-(4-methylpiperazin-1-yl)butan-1-one,
(R)-1-(3,4-dihydropyrazino[1,2-a]indol-2(1H)-yl)-2-methyl-3-(4-methylpiperazin-1-yl)propan-1-one,
(S)-1-(3,4-dihydropyrazino[1,2-a]indol-2(1H)-yl)-2-methyl-3-(4-methylpiperazin-1-yl)propan-1-one,
(S)-1-(3,4-dihydropyrazino[1,2-a]indol-2(1H)-yl)-3-(4-methylpiperazin-1-yl)butan-1-one,
(R)-1-(3,4-dihydropyrazino[1,2-a]indol-2(1H)-yl)-3-(4-methylpiperazin-1-yl)butan-1-one,
(R)-2-(4-cyclohexylpiperazin-1-yl)-1-((S)-3,4,10,10a-tetrahydropyrazino[1,2-a]indol-2(1H)-yl)propan-1-one, (S)-2-(4-cyclohexylpiperazin-1-yl)-1-((R)-3,4,10,10a-tetrahydropyrazino[1,2-a]indol-2(1H)-yl)propan-1-one,
(S)-2-(4-cyclohexylpiperazin-1-yl)-1-((S)-3,4,10,10a-tetrahydropyrazino[1,2-a]indol-2(1H)-yl)propan-1-one,
(R)-2-(4-cyclohexylpiperazin-1-yl)-1-((R)-3,4,10,10a-tetrahydropyrazino[1,2-a]indol-2(1H)-yl)propan-1-one,
1-(3,4-dihydropyrazino[1,2-a]indol-2(1H)-yl)-2-morpholinoethanone hydrochloride,
1-(3,4-dihydropyrazino[1,2-a]indol-2(1H)-yl)-2-(4-methylpiperazin-1-yl)ethanone hydrochloride,
1-(3,4-dihydropyrazino[1,2-a]indol-2(1H)-yl)-2-(dimethylamino)propan-1-one,
1-(3,4-dihydropyrazino[1,2-a]indol-2(1H)-yl)-2-(dimethylamino)propan-1-one maleate,
2-(4-acetylpiperazin-1-yl)-1-(3,4-dihydropyrazino[1,2-a]indol-2(1H)-yl)propan-1-one,
1-(3,4-dihydropyrazino[1,2-a]indol-2(1H)-yl)-2-((3S,5R)-3,5-dimethylpiperazin-1-yl)propan-1-one,
(3,4-dihydropyrazino[1,2-a]indol-2(1H)-yl)(1-(piperidin-1-yl)cyclopropyl)methanone,
(8-fluoro-3,4-dihydropyrazino[1,2-a]indol-2(1H)-yl)(1-(piperidin-1-yl)cyclopropyl)methanone,
1-(3,4-dihydropyrazino[1,2-a]indol-2(1H)-yl)-2-(9-methyl-3,9-diazaspiro[5.5]undecan-3-yl)propan-1-one,
(3,4-dihydropyrazino[1,2-a]indol-2(1H)-yl)(1-(4-methylpiperazin-1-yl)cyclopentyl)methanone,
(1-(4-methylpiperazin-1-yl)cyclopentyl)(3,4,10,10a-tetrahydropyrazino[1,2-a]indol-2(1H)-yl)methanone,
2-(piperazin-1-yl)-1-(3,4,10,10a-tetrahydropyrazino[1,2-a]indol-2(1H)-yl)propan-1-one,
2-(4-acetylpiperazin-1-yl)-1-(3,4,10,10a-tetrahydropyrazino[1,2-a]indol-2(1H)-yl)propan-1-one, and
1-(3,4-dihydropyrazino[1,2-a]indol-2(1H)-yl)-2-((3aR,6aS)-5-methylhexahydropyrrolo[3,4-c]pyrrol-2(1H)-yl)butan-1-one,
and a pharmaceutically acceptable salt, enantiomer, diastereomer, or racemate thereof.

21. A pharmaceutical composition comprising at least one compound according to claim 20, or a pharmaceutically acceptable salt, enantiomer, diastereomer or racemate thereof, and a pharmaceutically acceptable excipient.

22. A method for modulating sigma receptor activity in a subject, the method comprising administering to the subject a therapeutically effective amount of the compound according to claim 20, or a pharmaceutically acceptable salt, enantiomer, diastereomer or racemate thereof.

23. The method according to claim 22, wherein the subject suffers from a disease or condition selected from the group consisting of pain, diarrhea, hyperlipidemia, hypertriglyceridemia. hypercholesterolemia, obesity, migraine, arthritis, hypertension, arrhythmia, ulcer, glaucoma, tardive dyskinesia, stroke, epilepsy, stress, cancer, a learning deficit, a memory deficit, an attention deficit, an addiction to a drug, an addiction to a chemical substance, an inflammation disease, an autoimmune disease, a cognition disorder, a lipoprotein disorder, a neurodegenerative disease, a demyelinating disease, and a psychotic condition.

24. The method according to claim 23, wherein the pain is selected from the group consisting of neuropathic pain, inflammatory pain and a pain condition involving allodynia and/or hyperalgesia.

25. The method according to claim 23, wherein the addiction is to a drug or chemical substance selected from the group consisting of cocaine, amphetamine, ethanol and nicotine.

26. The method according to claim 23, wherein the stroke is ischemic stroke.

27. The method according to claim 23, wherein the psychotic condition is selected from the group consisting of depression, anxiety and schizophrenia.

28. A compound selected from the group consisting of:
2-(4-benzylpiperidin-1-yl)-1-(3,4-dihydropyrazino[1,2-a]indol-2(1H)-yl)ethanone hydrochloride,
2-(4-benzylpiperidin-1-yl)-1-(3,4-dihydropyrazino[1,2-a]indol1-2(1H)-yl)propan-1-one,
2-(4-benzylpiperidin-1-yl)-1-(10-methyl-3,4-dihydropyrazino[1,2-a]indol-2(1H)-yl)ethanone, and
a pharmaceutically acceptable salt, enantiomer, diastereomer or racemate thereof.

29. A pharmaceutical composition comprising at least one compound according to claim 28, or a pharmaceutically acceptable salt, enantiomer, diastereomer or racemate thereof, and a pharmaceutically acceptable excipient.

30. A method for modulating sigma receptor activity in a subject, the method comprising administering to the subject a therapeutically effective amount of the compound according to claim 28, or a pharmaceutically acceptable salt, enantiomer, diastereomer or racemate thereof.

31. The method according to claim 30, wherein the subject suffers from a disease or condition selected from the group consisting of pain, diarrhea, hyperlipidemia, hypertriglyceridemia, hypercholesterolemia, obesity, migraine, arthritis, hypertension, arrhythmia, ulcer, glaucoma, tardive dyskinesia, stroke, epilepsy, stress, cancer, a learning deficit, a memory deficit, an attention deficit, an addiction to a drug, an addiction to a chemical substance, an inflammation disease, an autoimmune disease, a cognition disorder, a lipoprotein disorder, a neurodegenerative disease, a demyelinating disease, and a psychotic condition.

32. The method according to claim 31, wherein the pain is selected from the group consisting of neuropathic pain, inflammatory pain and a pain condition involving allodynia and/or hyperalgesia.

33. The method according to claim 31, wherein the addiction is to a drug or chemical substance selected from the group consisting of cocaine, amphetamine, ethanol and nicotine.

34. The method according 31, wherein the stroke is ischemic stroke.

35. The method according to claim 31, wherein the psychotic condition is selected from the group consisting of depression, anxiety and schizophrenia.

* * * * *

UNITED STATES PATENT AND TRADEMARK OFFICE
CERTIFICATE OF CORRECTION

PATENT NO. : 9,963,453 B2
APPLICATION NO. : 14/786241
DATED : May 8, 2018
INVENTOR(S) : Ramón Merce-Vidal, José-Luís Díaz-Fernández and Carmen Almansa-Rosales It is certified that error appears in the above-identified patent and that said Letters Patent is hereby corrected as shown below:

On the Title Page

Column 2, item (56), OTHER PUBLICATIONS, Line 26, Ronsisvalle, et al. reference:
p. 1499-1609 should read --p. 1499-1509--.

Signed and Sealed this
Twenty-sixth Day of June, 2018

Andrei Iancu
*Director of the United States Patent and Trademark Office*